US009858464B2

(12) United States Patent
Piestun et al.

(10) Patent No.: US 9,858,464 B2
(45) Date of Patent: Jan. 2, 2018

(54) 3-D LOCALIZATION AND IMAGING OF DENSE ARRAYS OF PARTICLES

(71) Applicant: THE REGENTS OF THE UNIVERSITY OF COLORADO, Denver, CO (US)

(72) Inventors: Rafael Piestun, Boulder, CO (US); Anthony Barsic, Boulder, CO (US)

(73) Assignee: The Regents of the University of Colorado, A Body Corporate, Denver, CO (US)

(*) Notice: Subject to any disclaimer, the term of this patent is extended or adjusted under 35 U.S.C. 154(b) by 173 days.

(21) Appl. No.: 14/777,361

(22) PCT Filed: Mar. 14, 2014

(86) PCT No.: PCT/US2014/029391
§ 371 (c)(1),
(2) Date: Sep. 15, 2015

(87) PCT Pub. No.: WO2014/144820
PCT Pub. Date: Sep. 18, 2014

(65) Prior Publication Data
US 2016/0048963 A1 Feb. 18, 2016

Related U.S. Application Data

(60) Provisional application No. 61/791,392, filed on Mar. 15, 2013.

(51) Int. Cl.
G06K 9/00 (2006.01)
G06K 9/68 (2006.01)
(Continued)

(52) U.S. Cl.
CPC ............ *G06K 9/00* (2013.01); *G02B 21/361* (2013.01); *G02B 21/367* (2013.01);
(Continued)

(58) Field of Classification Search
CPC .......... G06K 9/00; G06K 9/6807; G06T 7/73; G06T 2200/04; G06T 2207/10016;
(Continued)

(56) References Cited

U.S. PATENT DOCUMENTS 3,054,898 A    9/1962   Westover et al.
3,597,083 A    8/1971   Fraser
(Continued)

FOREIGN PATENT DOCUMENTS

WO    WO2007116365 A2    10/2007

OTHER PUBLICATIONS

Zhu et al. "Faster STORM Using Compressed Sensing", Apr. 22, 2012.*
Written Opinion dated Jul. 22, 2014 as received in Application No. PCT/US2014/029391.
Search Report dated Jul. 22, 2014 as received in Application No. PCT/US2014/029391.
Chasles, F. et al., "Full-Field Optical Sectioning and Three-Dimensional Localization of Fluorescent Particles Using Focal Plane Modulation," Optics Letters, vol. 31, No. 9, May 1, 2006, 3 pgs.
Dowski, Jr., Edward R. et al., "Single-Lens Single-Image Incoherent Passive-Ranging Systems," Applied Optics, vol. 33, No. 29, Oct. 10, 1994, 12 pgs.
(Continued)

Primary Examiner — Aaron W Carter
(74) Attorney, Agent, or Firm — Maschoff Brennan

(57) ABSTRACT

Systems, methods, and computer program products are disclosed to localize and/or image a dense array of particles. In some embodiments, a plurality of particles may be imaged using an imaging device. A plurality of point spread function dictionary coefficients of the image may be estimated using a point spread function dictionary; where the point spread function dictionary can include a plurality of spread function responses corresponding to different particle positions. From the point spread function dictionary coefficients the number of particles in the image can be determined. Moreover location of each particle in the image can be determined from the point spread function dictionary coefficients.

24 Claims, 21 Drawing Sheets

(51) Int. Cl.
  *G06T 7/73* (2017.01)
  *G02B 21/36* (2006.01)
  *G01N 21/64* (2006.01)
  *G02B 21/14* (2006.01)

(52) U.S. Cl.
  CPC .............. *G06K 9/6807* (2013.01); *G06T 7/73* (2017.01); *G01N 21/6458* (2013.01); *G02B 21/14* (2013.01); *G06T 2200/04* (2013.01); *G06T 2207/10016* (2013.01); *G06T 2207/10056* (2013.01); *G06T 2207/10064* (2013.01); *G06T 2207/30242* (2013.01)

(58) Field of Classification Search
  CPC ........... G06T 2207/10056; G06T 2207/10064; G02B 21/0076; G01N 21/6458
  See application file for complete search history.

(56) References Cited

U.S. PATENT DOCUMENTS

| | | |
|---|---|---|
| 3,901,595 A | 8/1975 | Helava et al. |
| 3,961,851 A | 6/1976 | Gerharz |
| 4,178,090 A | 12/1979 | Marks et al. |
| 4,471,785 A | 9/1984 | Wilson et al. |
| 4,573,191 A | 2/1986 | Kidode et al. |
| 4,794,550 A | 12/1988 | Greivenkamp, Jr. |
| 4,825,263 A | 4/1989 | Desjardins et al. |
| 4,843,631 A | 6/1989 | Steinpichler et al. |
| 5,076,687 A | 12/1991 | Adelson |
| 5,102,223 A | 4/1992 | Uesugi et al. |
| 5,193,124 A | 3/1993 | Subbarao |
| 5,243,351 A | 9/1993 | Rafanelli et al. |
| 5,337,181 A | 8/1994 | Kelly |
| 5,521,695 A | 5/1996 | Cathey, Jr. et al. |
| 5,701,185 A | 12/1997 | Reiss et al. |
| 6,344,893 B1 | 2/2002 | Mendlovic et al. |
| 6,969,003 B2 | 11/2005 | Havens et al. |
| 7,342,717 B1 | 3/2008 | Hausmann et al. |
| 7,604,981 B1 | 10/2009 | Harris, Jr. et al. |
| 7,705,970 B2 | 4/2010 | Piestun et al. |
| 8,620,065 B2 | 12/2013 | Piestun et al. |
| 8,693,742 B2 | 4/2014 | Piestun et al. |
| 9,071,754 B2* | 6/2015 | Ishii .................. H04N 5/23248 |
| 2003/0035105 A1 | 2/2003 | Quist et al. |
| 2003/0061035 A1 | 3/2003 | Kadambe |
| 2003/0096220 A1 | 5/2003 | Lafferty et al. |
| 2004/0125373 A1 | 7/2004 | Oldenbourg et al. |
| 2005/0057744 A1 | 3/2005 | Pohle et al. |
| 2005/0174113 A1* | 8/2005 | Tsao .................. G01R 33/5611 324/307 |
| 2006/0126921 A1 | 6/2006 | Shorte et al. |
| 2007/0121107 A1 | 5/2007 | Tsai et al. |
| 2007/0130095 A1* | 6/2007 | Peot .................... G06T 3/4053 706/20 |
| 2007/0268366 A1 | 11/2007 | Raskar et al. |
| 2008/0137059 A1 | 6/2008 | Piestun et al. |
| 2009/0206251 A1 | 8/2009 | Hess et al. |
| 2009/0244090 A1 | 10/2009 | Zhang et al. |
| 2009/0324029 A1* | 12/2009 | Araikum .................. G06T 5/003 382/128 |
| 2010/0092086 A1* | 4/2010 | Lei ........................ G06T 5/003 382/173 |
| 2010/0278400 A1 | 11/2010 | Piestun et al. |
| 2011/0002530 A1 | 1/2011 | Zhuang et al. |
| 2011/0249866 A1 | 10/2011 | Piestun et al. |
| 2011/0254969 A1* | 10/2011 | Tyurina .............. G06K 9/00134 348/222.1 |
| 2011/0310226 A1 | 12/2011 | McEldowney |
| 2012/0029829 A1 | 2/2012 | Li et al. |
| 2012/0062708 A1 | 3/2012 | Johnson et al. |
| 2012/0182558 A1 | 7/2012 | Masumura |
| 2012/0273676 A1 | 11/2012 | Kuijper |
| 2013/0102865 A1 | 4/2013 | Mandelis et al. |
| 2013/0147925 A1 | 6/2013 | Lew et al. |
| 2013/0271592 A1* | 10/2013 | Piestun .................. H04N 7/18 348/79 |
| 2013/0294645 A1* | 11/2013 | Sibarita .............. G02B 21/0076 382/103 |
| 2013/0300912 A1* | 11/2013 | Tosic ........................ G06N 5/04 348/335 |
| 2014/0078566 A1 | 3/2014 | Rosen |
| 2014/0192166 A1 | 7/2014 | Cogswell et al. |
| 2014/0226881 A1 | 8/2014 | Piestun et al. |
| 2014/0346328 A1* | 11/2014 | Niu ...................... G02B 5/1842 250/225 |
| 2015/0035946 A1 | 2/2015 | Piestun et al. |
| 2015/0042783 A1* | 2/2015 | Ober .................. G02B 21/0032 348/80 |
| 2015/0192510 A1 | 7/2015 | Piestun et al. |
| 2016/0048963 A1 | 2/2016 | Piestun et al. |
| 2016/0125610 A1 | 5/2016 | Piestun |
| 2016/0231553 A1 | 8/2016 | Piestun et al. |
| 2016/0356746 A1* | 12/2016 | Piestun .............. G01N 21/1702 |

OTHER PUBLICATIONS

Greengard, Adam et al., "Depth From Diffracted Rotation," Optics Letters, vol. 31, No. 2, Jan. 15, 2006, 3 pgs.
Greengard, Adam et al., "Depth From Rotating Point Spread Functions," Proceedings of SPIE, vol. 5557, 2004, 7 pgs.
Greengard, Adam et al., "Fisher Information of 3D Rotating Point Spread Functions," Computational Optical Sensing and Imaging Presentation, Jun. 6, 2005, 31 pages.
Johnson, Gregory E. et al., "Passive Ranging Through Wave-Front Coding: Information and Application," Applied Optics, vol. 39, No. 11, Apr. 10, 2000, 11 pgs.
Juette, "Three-dimensional sub-1 00 nm resolution fluorescence microscopy of thick samples," 2008, Nat Methods 5: 3 pgs.
Kao, H. Pin et al., "Tracking of Single Fluorescent Particles in Three Dimensions: Use of Cylindrical Optics to Encode Particle Position," Biophysical Journal, vol. 67, Sep. 1994, 10 pgs.
Pavani, et al., "Three-dimensional, single-molecule fluorescence imaging beyond the diffraction limit by using a double-helix point spread function", PNAS, Mar. 3, 2009, and online published, Feb. 11, 2009, 5 pgs.
Pavani et al., "Three dimensional tracking of fluorescent microparticles using a photon-limited double-helix response system", Optics Express, 2008, 10 pgs.
Pentland, Alex Paul, "A New Sense for Depth of Field," IEEE Transactions on Pattern Analysis and Machine Intelligence, vol. PAMI-9, No. 4, Jul. 1987, 9 pgs.
Piestun, Rafael et al., "Wave Fields in Three Dimensions: Analysis and Synthesis," J. Opt. Soc. Am. A., vol. 13, No. 9, Sep. 1996, 12 pgs.
Sirat, Gabriel Y., "Conoscopic Holography. I. Basic Principles and Physical Basis," J. Opt. Soc. Am. A, vol. 9, No. 1, Jan. 1992, 14 pgs.
Subbarao, Murali et al., "Analysis of Defocused Image Data for 3D Shape Recovery Using a Regularization Technique," SPIE, vol. 3204, 1997, 12 pgs.
Thomann et al., "Automatic fluorescent tag detection in 3D with super-resolution: application to analysis of chromosome movement", J. of Microscopy, 2002, 16 pgs.
GB Examination Report, dated Feb. 12, 2015, as received in Application No. 1422460.4.
GB Examination Report Search Report, dated Jul. 6, 2015, as received in Application No. 1422460.4.
International Search Report and Written Opinion dated Feb. 6, 2014 in related PCT Application No. PCT/US13/47379.
International Search Report and Opinion, dated Dec. 12, 2014 in PCT Application No. PCT/US2014/052756.
International Search Report and Written Opinion dated Jan. 27, 2016 in PCT Application No. PCT/US2015/059331 (15 pages).
Vellekoop I.M., "Focusing coherent light through opaque strongly scattering media", Optics Letters, Aug. 15, 2007, vol. 32, No. 16.
Vellekoop I.M., "Demixing light paths inside disordered metamaterials", Optics Express, Jan. 7, 2008, vol. 16, No. 1.

(56) References Cited

OTHER PUBLICATIONS

X. Xu, "Time-reversed ultrasonically encoded optical focusing into scattering media", Nature Photonics 5, Jan. 16, 2011, 154-157.

K. Si., "Breaking the spatial resolution barrier via iterative sound-light interaction in deep tissue microscopy", Scientific Reports, Oct. 19, 2012.

Chaigne, T., "Controlling Light in Scattering Media Noninvasively Using the Photo-acoustic Transmission-matrix".

Conkey, D.B., "Genetic algorithm optimization for focusing through turbid media in noisy environments", Optics Express, Feb. 27, 2012, vol. 20, No. 5.

Conkey, D.B., "High-speed scattering medium characterization with application to focusing light through turbid media", Optics Express, Jan. 16, 2012, vol. 20, No. 2.

Yang, Xin, "Three-dimensional scanning microscopy through thin turbid media", Optics Express, Jan. 30, 2012, vol. 20, No. 3.

Popoff, S.M., "Measuring the Transmission Matrix in Optics: An Approach to the Study and Control of Light Propagation in Disordered Media", Physical Review Letters, Mar. 12, 2010, PRL 104, 100601.

Yaqoob, Z., "Optical phase conjugation for turbidity suppression in biological samples", Nat Photonics, Jun. 1, 2009.

Si, K., "Fluorescence imaging beyond the ballistic regime by ultrasound pulse guided digital phase conjugation", Nat Photonics, Oct. 1, 2012, 657-661.

Katz, O., "Focusing and compression of ultrashort pulses through scattering media", Nature Photonics 5, May 22, 2011, 372-377.

Judkewitz, B., "Speckle-scale focusing in the diffusive regime with time reversal of variance-encoded light", Nature Photonics, Mar. 17, 2013, 300-305.

Kong, F. "Photoacoustic-guided convergence of light through optically diffusive media", Opt. Lett. 36, 2053-5 (2011).

Aguet, Francois et al., "A Maximum-Likelihood Formalism for Sub-Resolution Axial Localization of Fluorescent Nanoparticles," Optics Express, vol. 13, No. 26, Dec. 26, 2005, 20 pgs.

\* cited by examiner

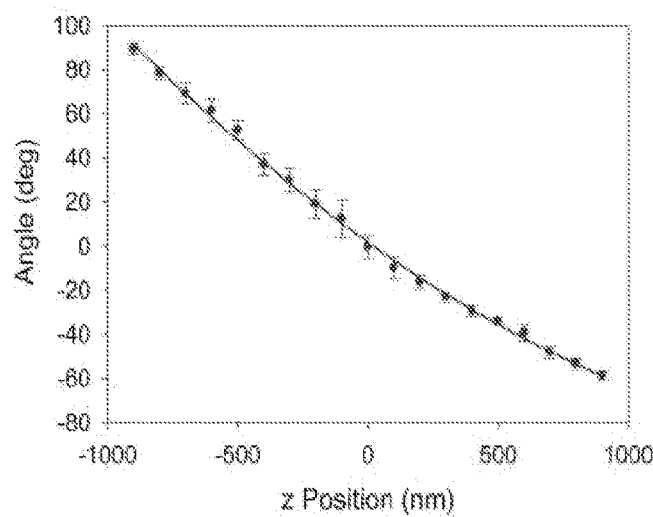
*Figure 4A*
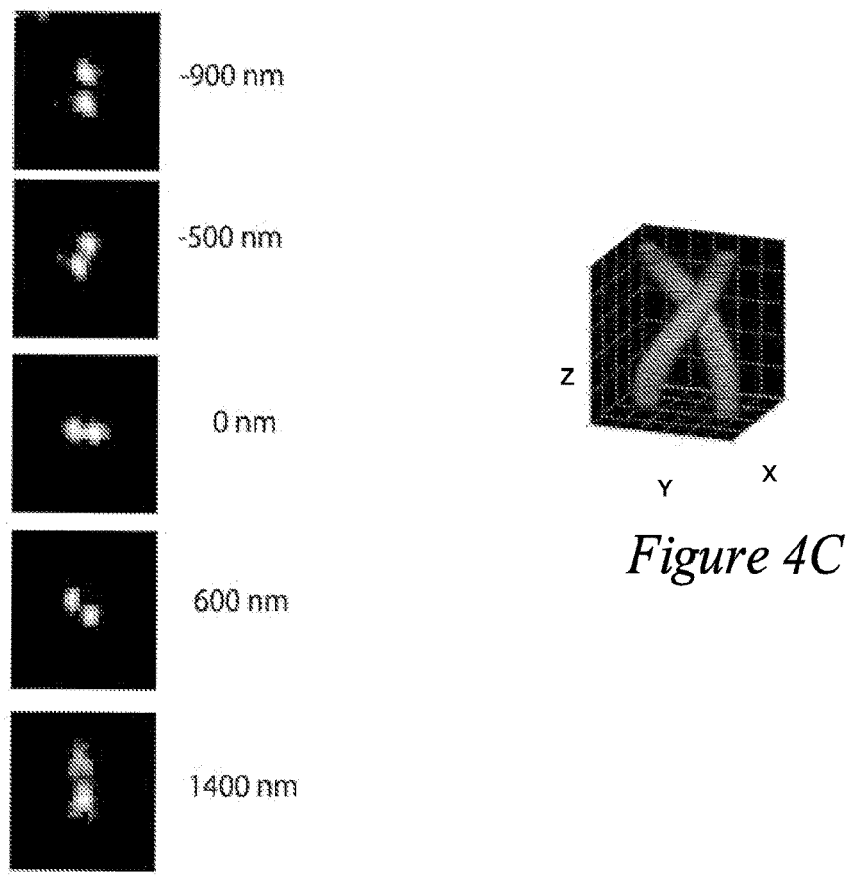
*Figure 4C*
*Figure 4B*

3-D LOCALIZATION AND IMAGING OF DENSE ARRAYS OF PARTICLES

BACKGROUND

The use of digital devices to collect and store irradiance patterns representative of the scene, optics, etc. has provided a convenient means for storing and processing images. Consequently, image processing algorithms combined with specialized optics are increasingly used to decode the sampled patterns into a form conveying the most relevant information to the user. Examples include, but are not limited to, using algorithms to remove optical aberrations and extract depth information encoded into the collected irradiance pattern.

SUMMARY

Embodiments include a method for detecting the number and location of particles. The method may include imaging a plurality of particles using an imaging system having a point spread function, wherein the imaging returns an image; estimating a plurality of point spread function dictionary coefficients of the image using a point spread function dictionary, wherein the point spread function dictionary includes a plurality of point spread function responses that each correspond with a different particle position; and determining the number and/or location of particles in the image from the point spread function dictionary coefficients.

In some embodiments, the method may further comprise determining a two-dimensional location of each particle in the image from the point spread function dictionary coefficients. In some embodiments, the method may further comprise determining a three-dimensional location of the particles in the image from the point spread function dictionary coefficients.

In some embodiments, the point spread function may change as a function of the axial location of the plurality of particles. In some embodiments the number of particles in the image may be determined from a number of non-zero point spread function dictionary coefficients. In some embodiments, the number of particles in the image may be determined from a number of point spread function dictionary coefficients above or below a threshold value.

In some embodiments, the point spread function dictionary may include a plurality of point spread function responses that correspond with a plurality of three-dimensional spatial position of the particle. In some embodiments, the point spread function dictionary may include a plurality of point spread function responses that correspond with a plurality of two-dimensional spatial position of the particle. In some embodiments, the point spread function may include a double helix point spread function. In some embodiments, the point spread function may include an astigmatic point spread function. In some embodiments, the point spread function may produce lobes in the image that are displaced based on the axial position of the plurality of particles. In some embodiments, the plurality of coefficients of the image of the particles are estimated using either or both a Matching Pursuit algorithm and a Convex Optimization algorithm. In some embodiments, the plurality of coefficients of the image of the particles may be estimated using an optimization algorithm.

Embodiments include a computer-implemented method for reconstructing images from compressively sensed data that includes expressing an image as a set of point spread function dictionary coefficients each one corresponding to a particular element of a point spread function dictionary, wherein each particular element of the point spread function dictionary may be an image of an imaging system point spread function associated with a particular spatial position within a particular field of view. In some embodiments, each one of the set of point spread function dictionary coefficients may be calculated based on an optimization algorithm selected from the list consisting of Convex Optimization; Matching Pursuit; orthogonal Matching Pursuit; maximum likelihood estimation; Bayesian information criteria, maximum-likelihood principle; maximum-posterior estimator principle; maximum entropy principle; and minimum discrimination.

Embodiments include an imaging system. The imaging system may include a plurality of optical elements, an imager, a memory, and a processor. The plurality of optical elements may be configured to image a plurality of particles, wherein the optical elements generate a point spread function, and wherein the point spread function changes as a function of the axial location of the plurality of particles. The imager may be configured to image the plurality of particles located onto an image plane. The memory may include a point spread function dictionary that includes a plurality of point spread function responses that each correspond with a different particle position. The processor may be configured to estimate a plurality of point spread function dictionary coefficients of an image of the plurality of particles using the point spread function dictionary and determine the number and/or position of particles in the image using the point spread function dictionary coefficients.

In some embodiments, the processor may be further configured to determine a two-dimensional location of the plurality of particles in the image from the point spread function dictionary coefficients. In some embodiments, the number of particles in the image may be determined from the number of non-zero point spread function dictionary coefficients.

In some embodiments, the number of particles in the image may be determined from a number point spread function dictionary coefficients above or below a threshold value. In some embodiments, the point spread function produces lobes in the image that are displaced based on the axial position of the plurality of particles. In some embodiments, the point spread function dictionary may include a plurality of point spread function responses that correspond with a three-dimensional spatial position of the particle. In some embodiments, the point spread function dictionary may include a plurality of point spread function responses that correspond with a two-dimensional spatial position of the particle. In some embodiments, the plurality of point spread function dictionary coefficients of the image of the particles are estimated using a Matching Pursuit algorithm.

In some embodiments, the plurality of point spread function dictionary coefficients of the image of the particles are estimated based on an optimization algorithm selected from the list consisting of Convex Optimization; Matching Pursuit; orthogonal Matching Pursuit; maximum likelihood estimation; Bayesian information criteria, maximum-likelihood principle; maximum-posterior estimator principle; maximum entropy principle; and minimum discrimination.

Embodiments include a method for detecting the number and/or location of particles. The method may include imaging a plurality of particles using a point spread function that changes as a function of the axial location of a particle, wherein the imaging returns an image; estimating a first plurality of point spread function dictionary coefficients of the image using a Matching Pursuit algorithm with a first point spread function dictionary that includes a plurality of point spread function responses corresponding to a different particle position; determining a first region within which the particles are located in the image from the first plurality of point spread function dictionary coefficients; estimating a second plurality of point spread function dictionary coefficients of the image using a Convex Optimization algorithm with a second point spread function dictionary that includes a plurality of point spread function responses corresponding to different particle position; and determining a location of the particles in the image from the second plurality of coefficients.

In some embodiments, the number of point spread function responses in the second point spread function dictionary may be greater than the number of point spread function responses in the first point spread function dictionary. In some embodiments, the spatial resolution of the point spread function responses in the second point spread function dictionary may be greater than the spatial resolution of the point spread function responses in the first point spread function dictionary.

In an aspect, a method for resolving at least one of a number and location of particles within a scene as described in at least one of the specifications and figures is disclosed.

In an aspect, a method for determining at least one of a number and location of particles located closer than the diffraction limit as described in at least one of the specifications and figures is disclosed.

In an aspect, a computer-implemented method for localizing labels within a scene is disclosed. The method may include expressing an image of the scene as a set of coefficients, each one corresponding to a particular element of a point spread function dictionary, wherein each particular element of the point spread function dictionary is an image of an imaging system point spread function (point spread function) associated with a particular 2-D or 3-D spatial position within a particular field of view, wherein the image of the scene is a superposition of the elements of the point spread function dictionary with the corresponding coefficients.

In an aspect, a computer-implemented method for reconstructing images from compressively sensed data is disclosed. The method may include expressing an image as a set of coefficients, each one corresponding to a particular element of a point spread function dictionary, wherein each particular element of the point spread function dictionary is an image of an imaging system point spread function (point spread function) associated with a particular spatial position within a particular field of view.

DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. When only the first reference label is used in the specification, the description is applicable to any one of the similar components having the same first reference label irrespective of the second reference label.

FIG. 4A illustrates an example calibration plot of angle versus z position of a particle imaged using a double-helix point spread function according to some embodiments described herein.

FIG. 4B also shows actual double-helix point spread function images taken from a fluorescent bead at different z positions illustrating the type of data used to extract the calibration plot according to some embodiments described herein.

FIG. 4C illustrates a simulation of the three-dimensional shape of the double-helix point spread function according to some embodiments described herein.

DETAILED DESCRIPTION

Figures 1A, 1B:
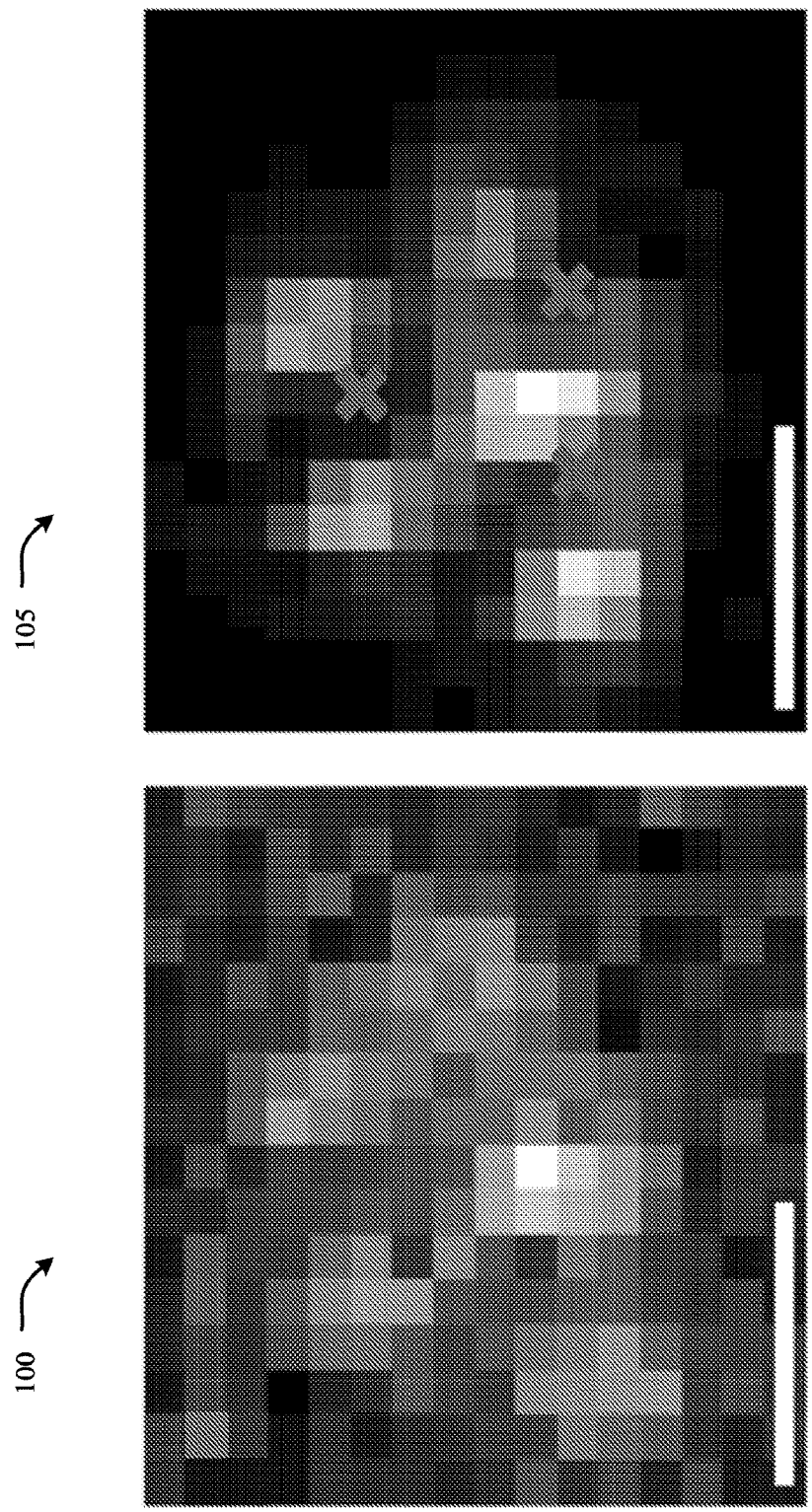
FIG. 1A is an example of raw data of overlapping particle images imaged using a double-helix point spread function according to some embodiments described herein.
FIG. 1B is an example image reconstructed from the image in FIG. 1A using embodiments described herein.

Embodiments of the present disclosure are directed towards various measurement techniques and/or processing algorithms to determine a number and/or location of particles. As used herein a particle may include a molecule, atom, small object, reflector, cell, scatterer, absorber, emitter, reflector, etc.

In some embodiments, this may be done with precision. In some embodiments, this may be done for particles that may be densely packed. In some embodiments, a super-resolution image may be collected in a fraction of the number of frames of conventional systems.

Embodiments of the present disclosure may be used in a number of applications. For example, embodiments of the present disclosure may be used in fluorescence imaging, astronomical observations, military applications, or scientific measurements. Still other applications are possible as well.

With the advent of digital computers, the purpose of optical imaging systems has changed. A primary goal may no longer be to produce the best image. Rather, a primary goal may be to produce the most useful data, which can be processed using computational methods to directly provide answers to various questions such as: What objects make up the scene under observation? How many of each type of object are there? What are their locations? How much noise is present in the data, and what would the data look like if the noise were not present? It is contemplated that the various measurement techniques and processing algorithms described herein may be capable of providing answers to questions of these sorts.

For example, one field in which the above sorts of questions, and the various measurement techniques and processing algorithms described herein, may be particularly applicable is the field of super-localization microscopy. In this paradigm, the object is assumed to consist of a collection of point sources which are observed using an imaging system. Classical descriptions of optical systems suggest the resolution capability of the system to be limited by the wavelength of light and the numerical aperture. With the best lenses available today, this works out to be approximately half a wavelength. This limit arises from the fact that diffraction does not allow light to be focused to or on an infinitesimally small spot. The pattern that arises from propagation through an optical system is called the system's point spread function, also known as the system's impulse response. If one observes an isolated point source, and the system point spread function is known, the image of the point spread function can be fit to "high" precision, and thus the location of that particle can be known or derived with a precision that is orders of magnitude better than the diffraction limit.

Microscopy techniques such as Photo-Activated Localization Microscopy (PALM) and Stochastic Optical Reconstruction Microscopy (STORM) leverage this idea. In these cases, super-resolution may be obtained by precisely localizing labels in the sample using knowledge of the system's point spread function. To reconstruct a clear image, labeling density should be defined so that details of the object may be identified. However, localization techniques dictate the individual particles to be well-separated from neighboring particles. To address this issue, experimental techniques employed in PALM and STORM enable the experimenter to excite a "small" subset of the particles per frame. However, many localizations from numerous frames may be combined to make or form a dense, super-resolved image. Enhanced spatial resolution may thus be achieved at the expense of temporal resolution. The present disclosure addresses these and other issues. In particular, the various measurement techniques and processing algorithms described herein may enable localization of significantly denser scenes of particles, which allow a super-resolution image to be collected in a fraction of the number of frames.

The reconstruction techniques of the present disclosure are based upon the realization that all the images collected consist of collections of images of the system's point spread function corrupted to a certain degree by noise. It is contemplated that an image may be decomposed using a point spread function dictionary or database that includes shifted point spread functions, and thus we determine the locations and strengths of the sources in the scene, while omitting the noise at this stage. An example of the point spread function dictionary or database of the present disclosure is discussed in further detail below in connection with at least FIG. 12 and FIG. 13. Furthermore, by posing the computational problem differently, we can avoid an issue of only observing well-resolved sources. Rather than taking a single image of a lone particle and fitting it to the system point spread function, the reconstruction technique of the present disclosure may examine a "small" window of the data and decompose it to a set of coefficients corresponding to each particle in the scene. It has been contemplated that there may be a number of ways to arrive at this decomposition. In particular, it has been contemplated that a Matching Pursuit (MP) technique and a Convex Optimization (CO) technique may be effective decomposition techniques. Other embodiments are possible as well.

With respect to the MP technique, the image is decomposed by iteratively selecting the "brightest" sources in the scene, until all sources have been retrieved. In general, the source locations and intensities may be found by projecting the data onto a basis set that consists of all possible particle images. In example embodiments, the "brightest" source will have the largest coefficient when it is projected onto the basis element that corresponds to its image; this location is stored, and that component is subtracted from the image. This continues until all sources have been found, and only background noise remains.

FIG. 1A is an example image 100 of raw data of overlapping particle imaged using a double-helix point spread function according to some embodiments described herein. As shown, the overlapping particles and noise create an image that is not easily decipherable. FIG. 1B is an example reconstructed image 105 that is reconstructed from the image 100 in FIG. 1A using embodiments described herein. The reconstructed image 105 also includes three red Xs indicating the estimated location of the particles. The reconstructed image 105 also has less noise and shows the lobes of the double-helix point spread function. Various techniques, algorithms, systems, processes, and/or methods are described herein to create the reconstructed image 105 from the image 100.

Figure 2:
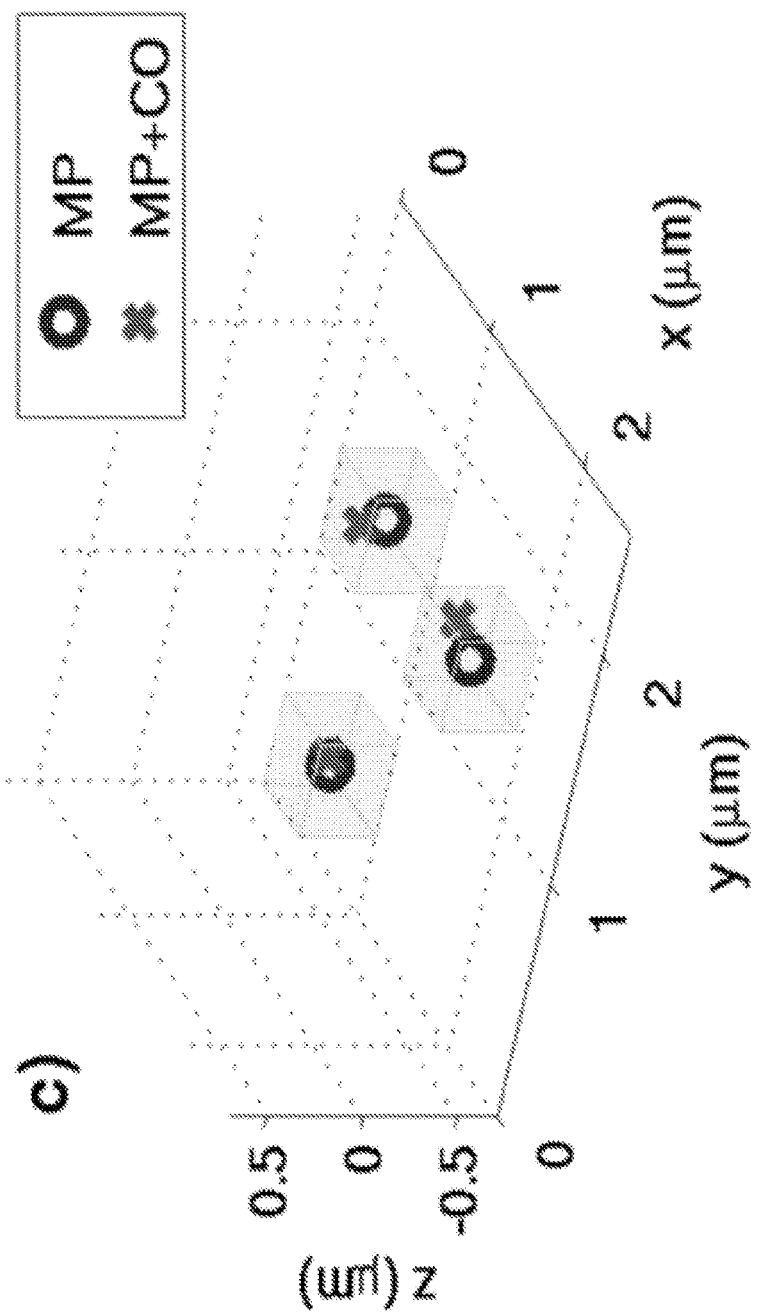
FIG. 2 shows the estimated locations of the particles imaged in FIG. 1A according to some embodiments described herein.

FIG. 2 shows the estimated locations of the particles imaged in FIG. 1A using embodiments described herein. The results using two different techniques are shown. MP represents the estimated location of the particles using the MP technique; and MP+CO represents the estimated location of the particles using both the MP technique and the CO technique. Although only these two techniques are shown, various other techniques may be used.

Figure 3:
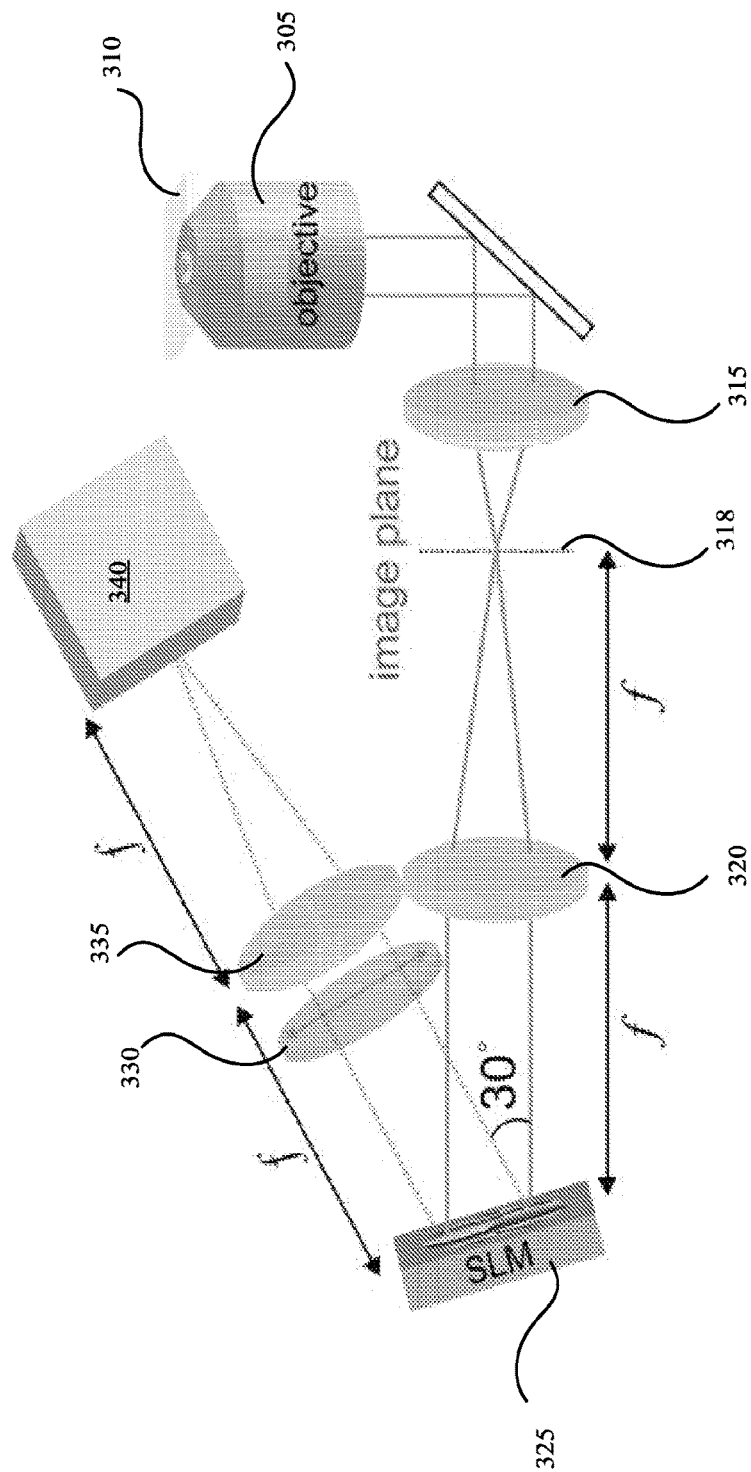
FIG. 3 illustrates an example imaging system for imaging particles using a point spread function according to some embodiments described herein.
Figure 20:
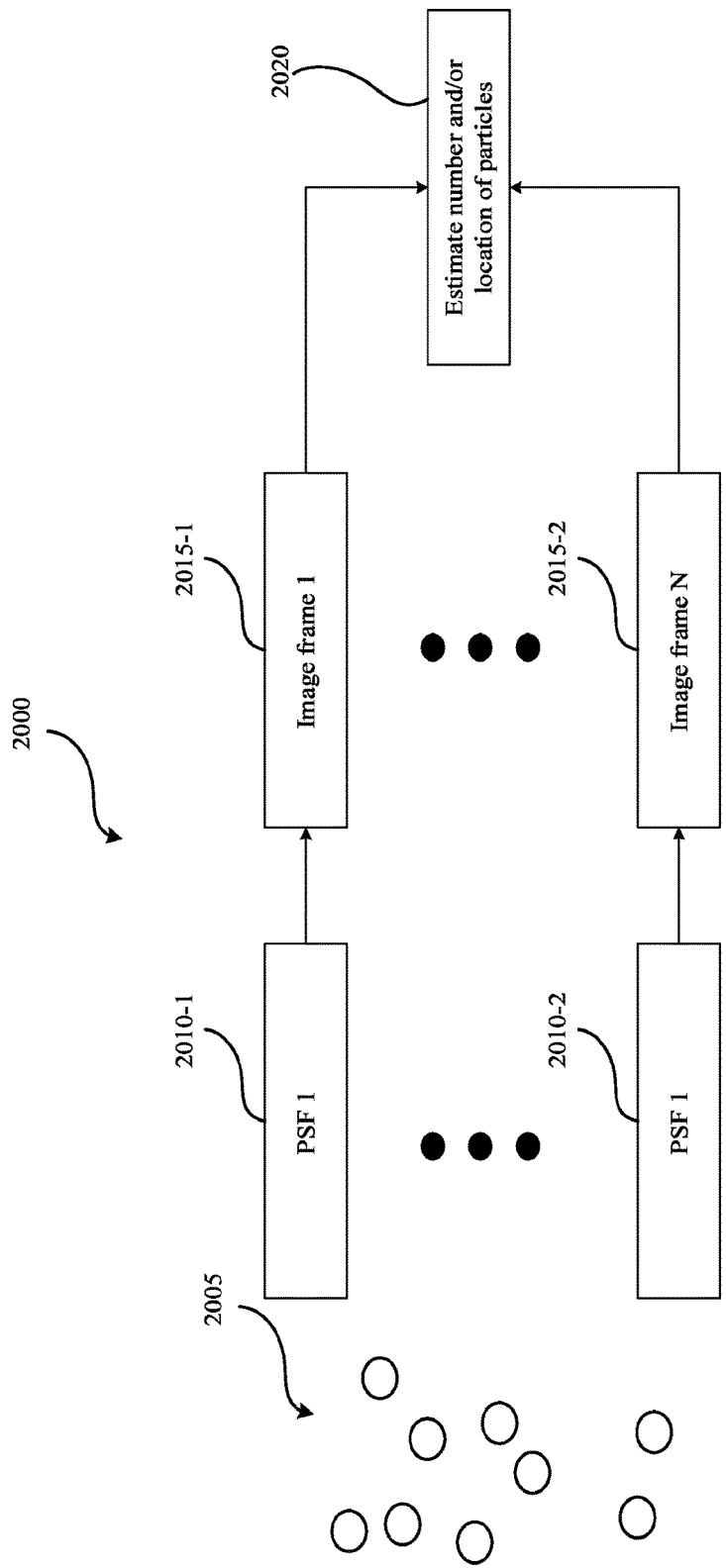
FIG. 20 illustrates an example imaging system process for imaging particles using a point spread function according to some embodiments described herein.

FIG. 3 illustrates an example imaging system 300 for imaging particles using a point spread function according to some embodiments described herein. Various other imaging systems may be used and/or the imaging system 300 may include any number of additional and/or alternative components, for example, as shown in FIG. 20 and/or FIG. 21. Any reference made herein to FIG. 3 may also extend to either or both FIG. 20 and FIG. 21. Furthermore, some components described in any of these figures may be removed other components added, and some components exchanged for other components. In some embodiments, all or portions of FIG. 3 may be part of a conventional imaging system. In some embodiments, a mask can be placed on any location within an imaging system.

In some embodiments, the 3-D positions of particles may be estimated using a wide-field fluorescence image using the double-helix point spread function shown in the figure. The imaging system 300, for example, can be composed of a sample located at an objective focal plane 310 of a microscope objective 305, a lens 315 with an image plane 318 (e.g., a conventional microscope), another lens 320, and an optical signal processing section.

The signal processing section can be essentially a 4f imaging system with a reflective phase-only spatial light modulator 325 placed in the Fourier plane. In some embodiments, an tube lens 315 (e.g., a achromatic lens) can be placed at a distance $f$ from the microscope's image plane 318 producing the Fourier transform of the image at a distance $f$ behind the lens. The phase of the Fourier transform can be modulated by reflection from the liquid crystal spatial light modulator 325. The spatial light modulator can include a double-helix point spread function. Because the spatial light modulator 325 can be sensitive only to vertically polarized light, a vertical polarizer 330 can be placed immediately after the spatial light modulator 325 to block any horizontally polarized light not modulated by the spatial light modulator 325. The final image can be produced by another achromatic lens 335 (e.g., $f=15$ cm) placed at a distance $f$ after the spatial light modulator 325 and recorded with a camera 340 (e.g., an EMCCD camera).

Additionally or alternatively, the spatial light modulator 325 may include or be replaced by a phase mask, an amplitude mask, or a phase/amplitude mask located in a Fourier plane or other plane. Moreover, in some embodiments, the imaging system 300 may be reconfigured with a refractive spatial light modulator. In some embodiments, the spatial light modulator 325 may produce a spatially varying phase delay, have a continuously varying phase, and/or may include a piecewise constant phase, a piecewise linear phase function, a continuous piecewise linear phase function or a convex piecewise linear phase function, and/or a discontinuous piecewise linear phase function.

In some embodiments, the imaging system 300 may include a refractive, reflective, or diffractive optical element composed of at least one linear phase domain (phase ramp) such that each linear phase domain is organized to generate a linear phase delay to light passing through one part of the objective. Each linear phase domain, for example, may have equal or different linear variations, including equal or different slope orientations.

When the spatial light modulator 325 is loaded with a double-helix point spread function phase-mask, the Fourier transform of the sample image can be multiplied by the double-helix point spread function transfer function. Equivalently, every object point may be convolved with two lobes. In some embodiments, the angular orientation of the two lobes may vary depending on the axial location of the object above or below focus. For example, the two lobes may be aligned horizontally when the particle is in focus. As the particle is moved towards the objective, the double-helix point spread function lobes may rotate in the counterclockwise direction. On the other hand, if the particle is moved away from the objective, the lobes may rotate in the clockwise direction.

Alternatively or additionally, a lateral point spread function may be used causing the lobes to be displaced horizontally depending on the axial location of the particle. For example, the two lobes may be aligned vertically when the particle is in focus. As the particle is moved towards the objective, a first lobe may move to the left and a second lobe may move to the right. On the other hand, if the particle is moved away from the objective, the first lobe may move to the right and the second lobe may move to the left.

In some embodiments, the point spread function may produce a transverse profile composed of multiple patterns. Each of these patterns may retain its fundamental shape with defocus yet each pattern may move in different trajectories during defocus.

In some embodiments, the point spread function may produce two image lobes that are separated from each other along a straight line. The two lobes may be separated from each other (e.g., the line may extend or contract) based on the defocus of the particles. For example, the two lobes may be separated from each other in the opposite direction.

In some embodiments, the point spread function may produce two lobes that move along two different straight lines as the particle moves relative to the objective lens from a positive defocus position to a negative defocus position and vice versa. In some embodiments, the two straight lines may be parallel to each other.

In some embodiments, the point spread function may have at least one helix with infinite offset radius that degenerates into a straight line. In some embodiments, the point spread function may have two straight lines with an axis of symmetry coinciding with the optical axis of the system. In some embodiments, the point spread function may have at least a helix with null (zero) pitch such that the helix degenerates into a circle or an ellipse. In some embodiments, the point spread function may generate a conical surface in three-dimensional space. In some embodiments, the point spread function may have at least one helix degenerating into a conical section curve.

In some embodiments, a maximum of a point spread function may describe a curve in three-dimensional space that turns around an axis at a constant or continuously varying distance (offset) while moving in the direction parallel to the axis. In some embodiments, a maximum of the point spread function describes a curve in three-dimensional space similar to a helix with varying offset from a helix axis and/or a pitch, and when both the axis and offset are constant, the point spread function describes a helical curve.

In some embodiments, the imaging system 300 may encode spectral and/or polarization information about each particle and/or the image.

In some embodiments, the imaging system 300 may include a converging lens such as, for example, a kinoform.

In some embodiments, the imaging system 300 may be configured to obtain at least two images with different focus settings. In some embodiments, the imaging system 300 may be configured to work either in a wide field mode or a confocal mode.

When a sample comprises multiple sparse particles at different 3-D positions, the detected double-helix point spread function image may exhibit two lobes (with different angular orientations) for each particle. The transverse (x-y) position of a particle may be estimated from the midpoint of the line connecting the positions of the two lobes, and the axial position can be estimated from the angle of the line connecting the two lobes using a calibration plot that maps angles to axial positions.

Some embodiments described herein may include a mechanism that produces a spatially varying phase difference imposed among different components of the light coming through different parts of the objective 305 to generate a three-dimensional point spread function image. Such a mechanism may be placed within the optical path of the objective 305 and/or the camera 340 and the image plane 318.

An example calibration plot of angle versus z position is shown in FIG. 4A for embodiments using a double-helix point spread function. Other calibration plots may also be used for other point spread functions. As shown in the plot, the position of the particle may vary as the rotation of the two lobes. In other examples, a similar plot may be constructed where the y-axis represents lateral separation rather than an angular rotation. FIG. 4C illustrates a simulation of the three-dimensional shape of the double-helix point spread function and shows how angular rotation may correspond to axial distance. FIG. 4B shows actual double-helix point spread function images taken from a fluorescent bead at different z positions illustrating the rotation of the lobes. In this example, the beads (pumped with 514 nm) have an emission spectrum with a peak at about 580 nm.

Figure 5:
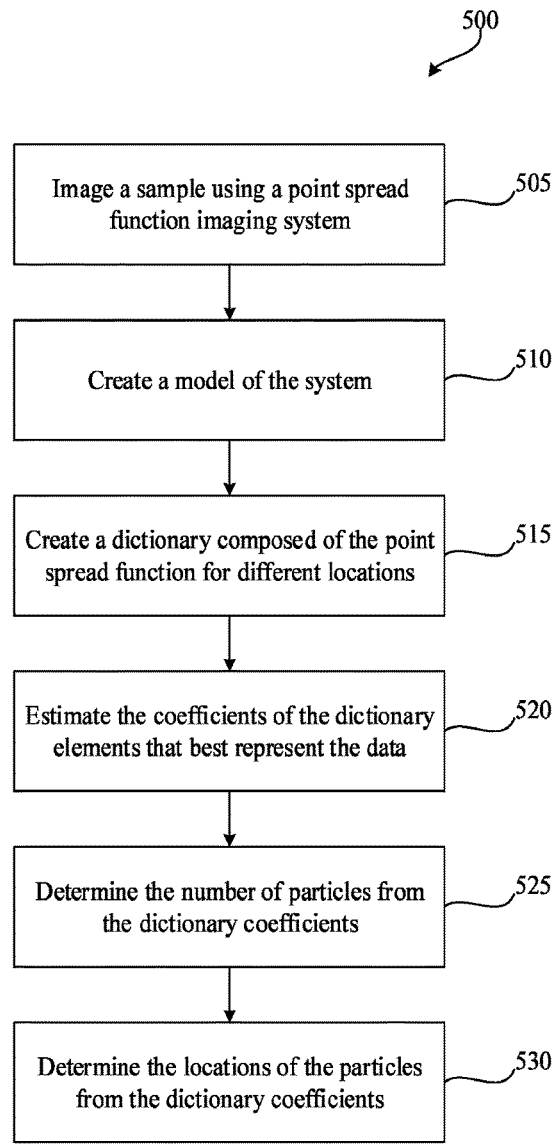
FIG. 5 is a flowchart of a process for determining the location of particles within a scene according to some embodiments described herein.

FIG. 5 is a flowchart of a process 500 for determining the location of particles within a scene according to some embodiments described herein. The process 500 starts at block 505. At block 505, a sample is imaged using a point spread function imaging system. The sample may be imaged, for example, using the imaging system 300 shown in FIG. 3. The spatial light modulator 325 may include the point spread function. Various types of point spread functions may be used including double-helix point spread function, a horizontal point spread function, a vertical point spread function, an astigmatic point spread function, a bifocal point spread function, and a lateral point spread function. In some embodiments, any point spread function may be used the produces lobes that are displaced based on the axial position of an imaged particle.

At block 510 a model of the imaging system may be created. In some embodiments, the model of the imaging system may be created prior to imaging. In some embodiments, the model of the imaging system may occur during calibration, during set up, during development, and/or during manufacturing. In some embodiments, the model may be created from experimental measurements, theoretical calculations, and/or a combination of both. In some embodiments, the model may vary depending on the type and/or the characteristics of the point spread function of the imaging system.

In some embodiments, a model of the system may be a mathematical description of the response of the system that relates output signals to input signals. The model may be the result of a theoretical calculation of the response based on the individual components and obtained through geometrical optics, wave optics, and/or rigorous electromagnetic calculations. The model may be obtained experimentally and/or may be composed of the measurements performed of the system response, possibly with interpolation between measurements and possibly with processing to reduce the influence of noise. In some embodiments the model may include a model of the noise which can also be based on measurements or theoretical.

Figure 12:
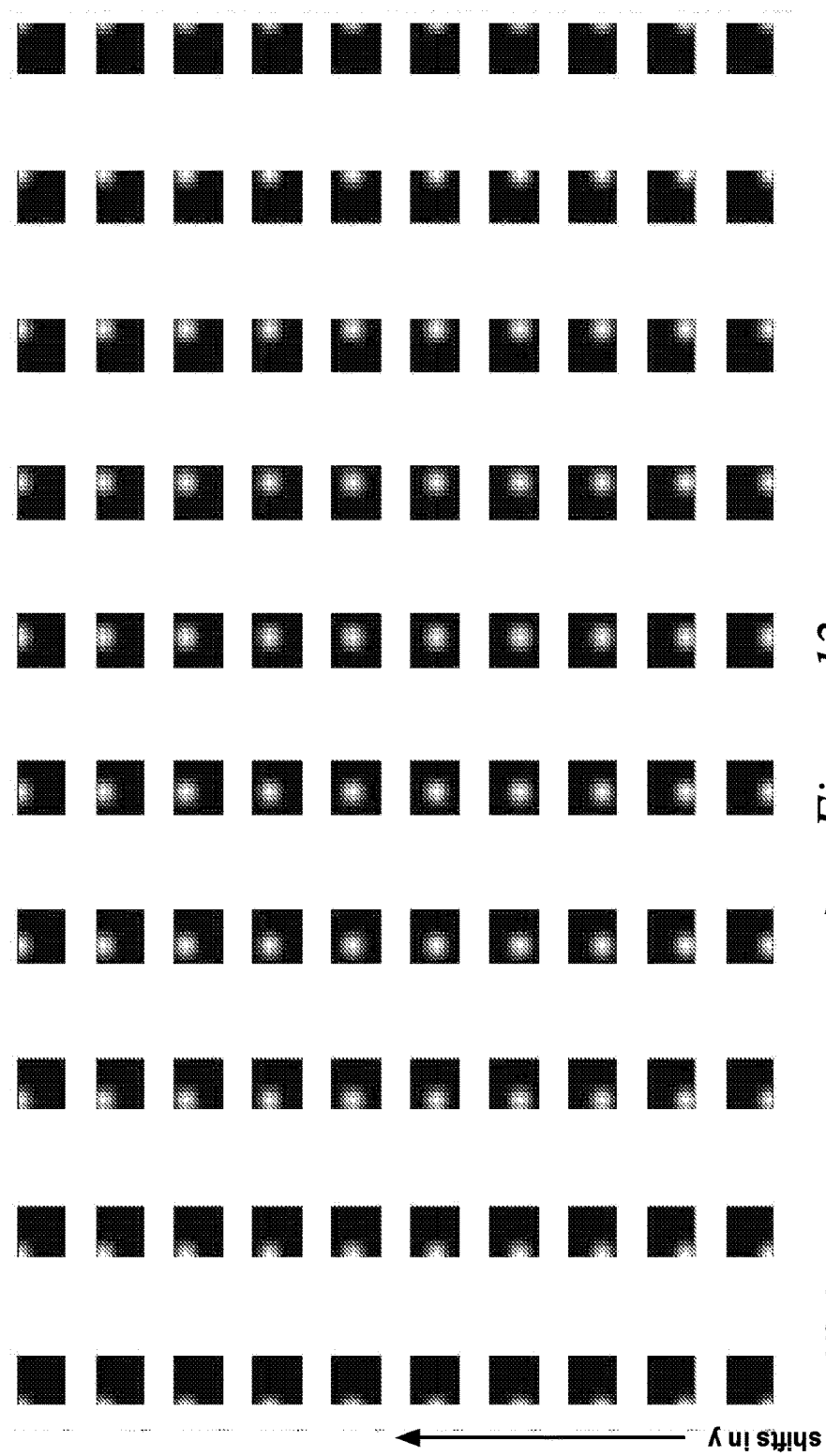
FIG. 12 illustrates an example 2-D point spread function basis point spread function dictionary, with x-y representation, for localization with arbitrary precision according to some embodiments described herein.
Figure 13:
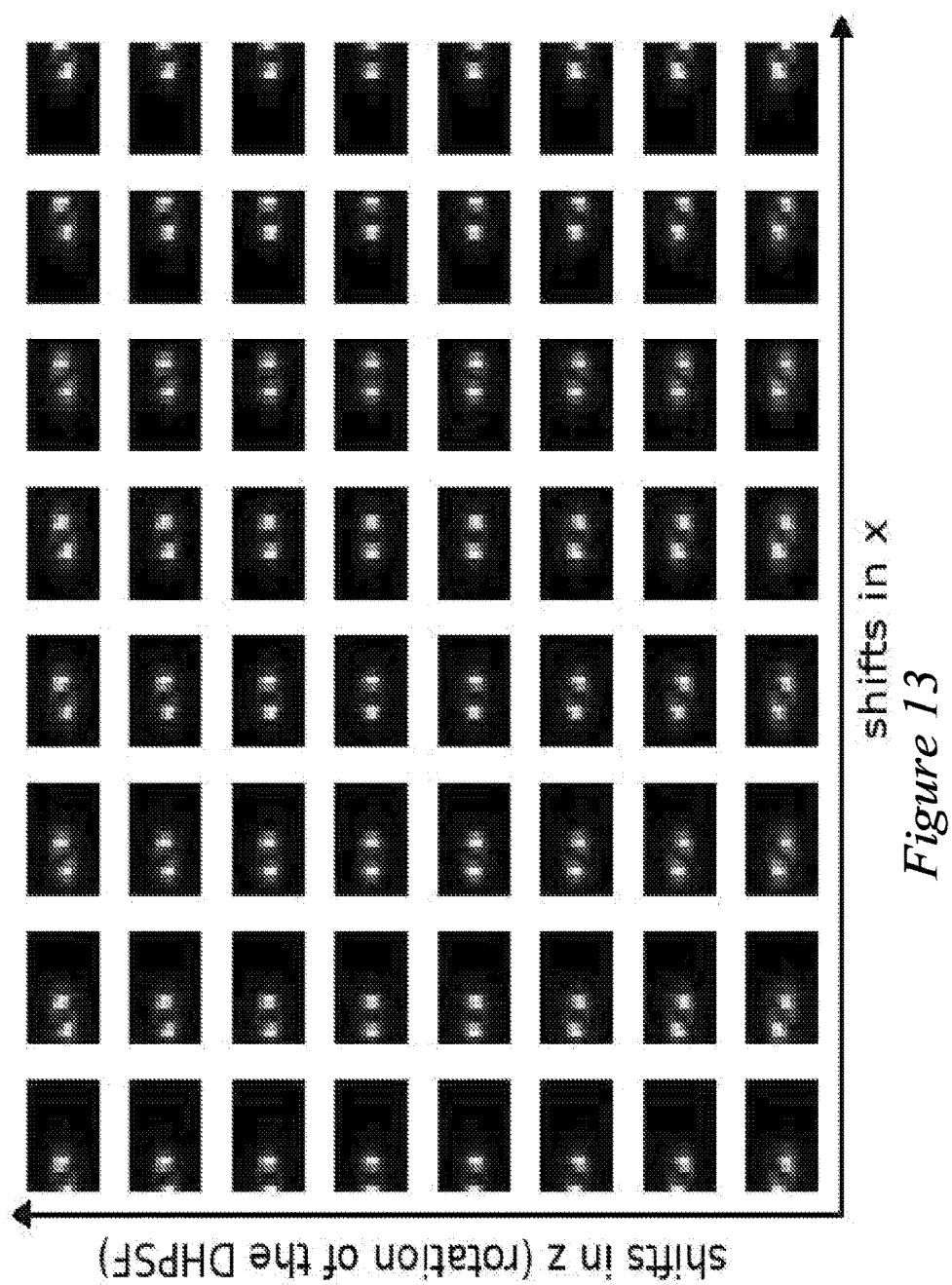
FIG. 13 illustrates 3-D point spread function basis point spread function dictionary, with x-z representation, for localization with arbitrary precision according to some embodiments described herein.
Figure 14:
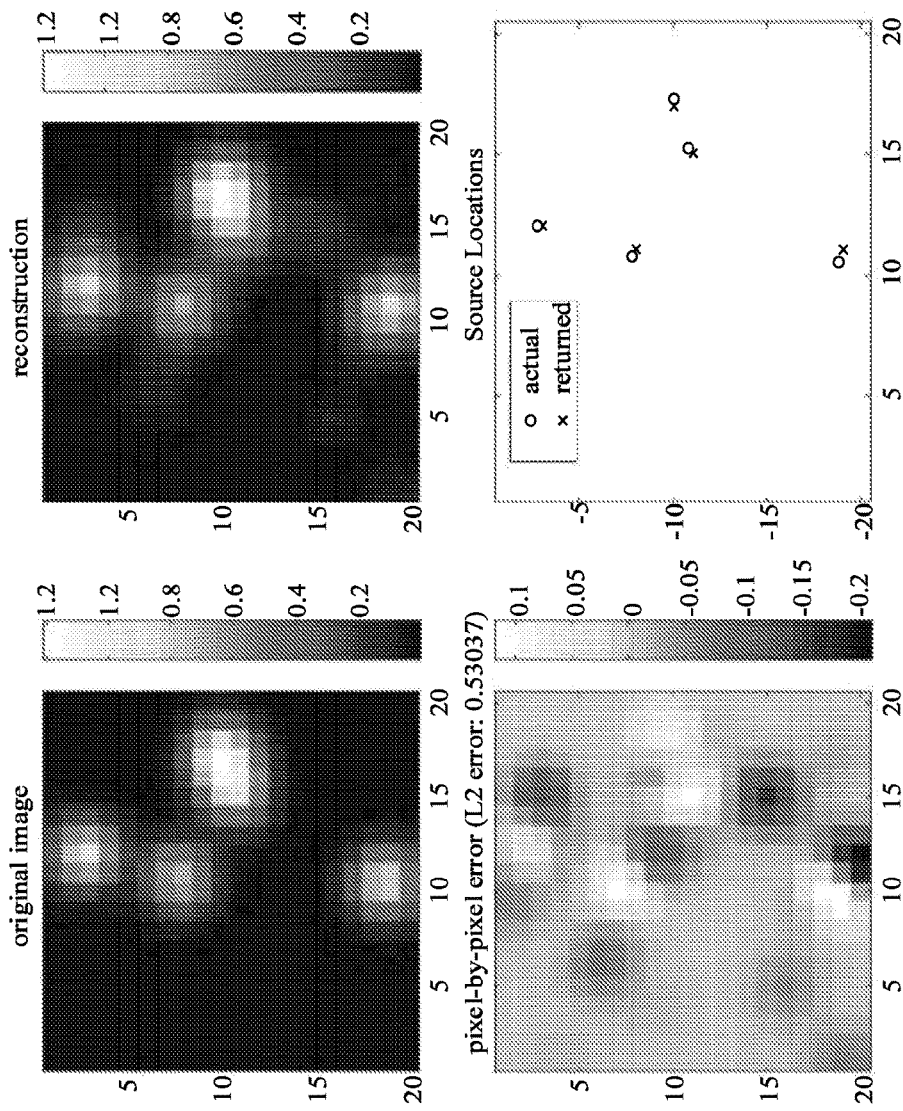
FIG. 14 illustrates an example of standard localization results according to some embodiments described herein.
Figure 15:
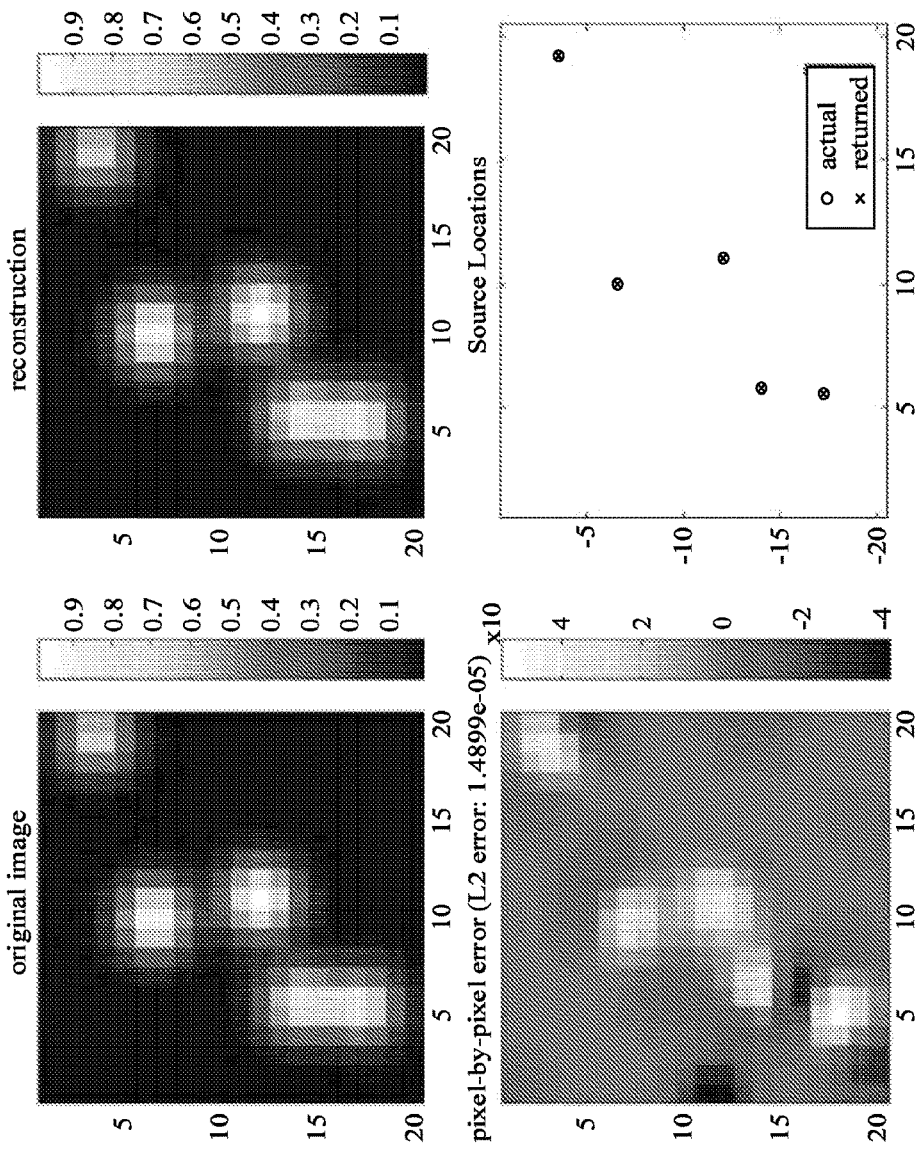
FIG. 15 illustrates an example of super-localization results according to some embodiments described herein.
Figure 16:
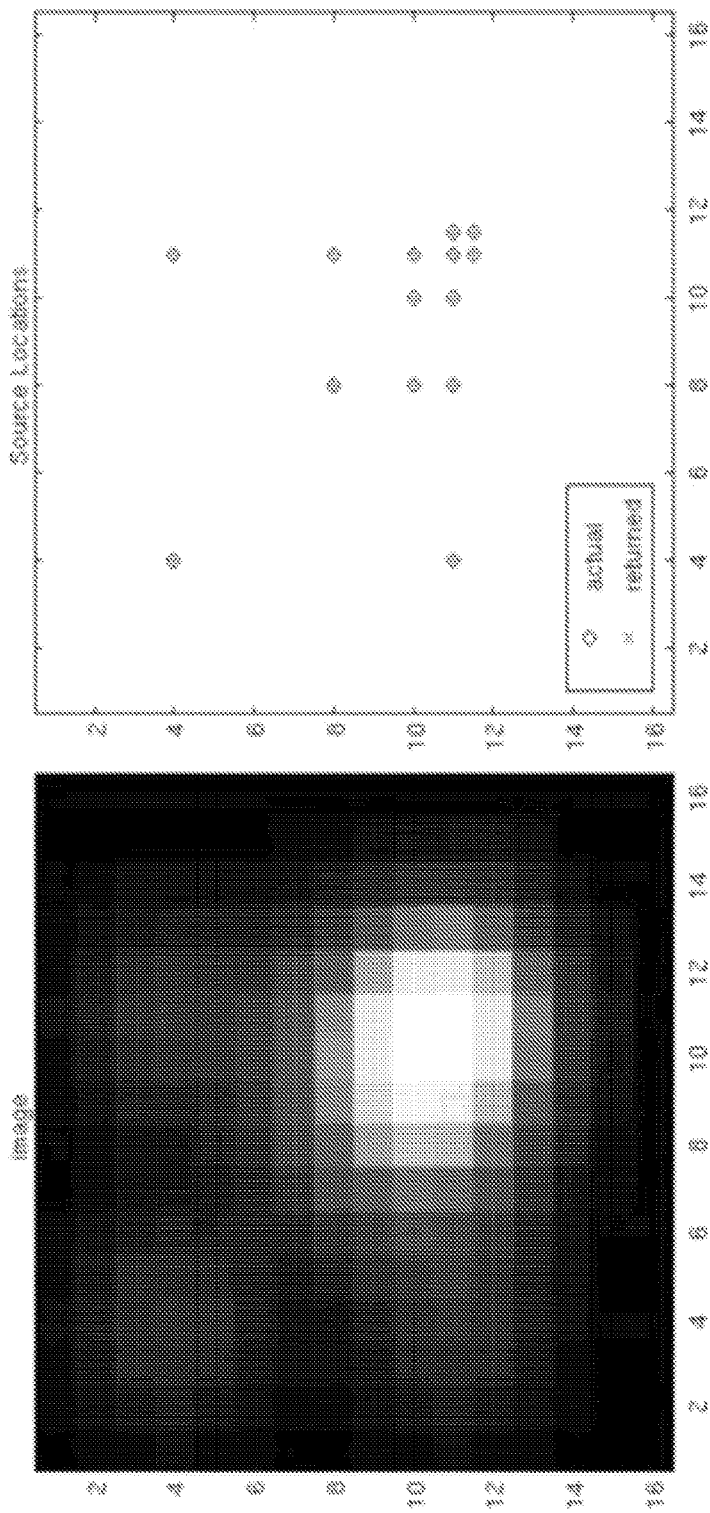
FIG. 16 illustrates an example of super-resolution results according to some embodiments described herein.
Figure 17:
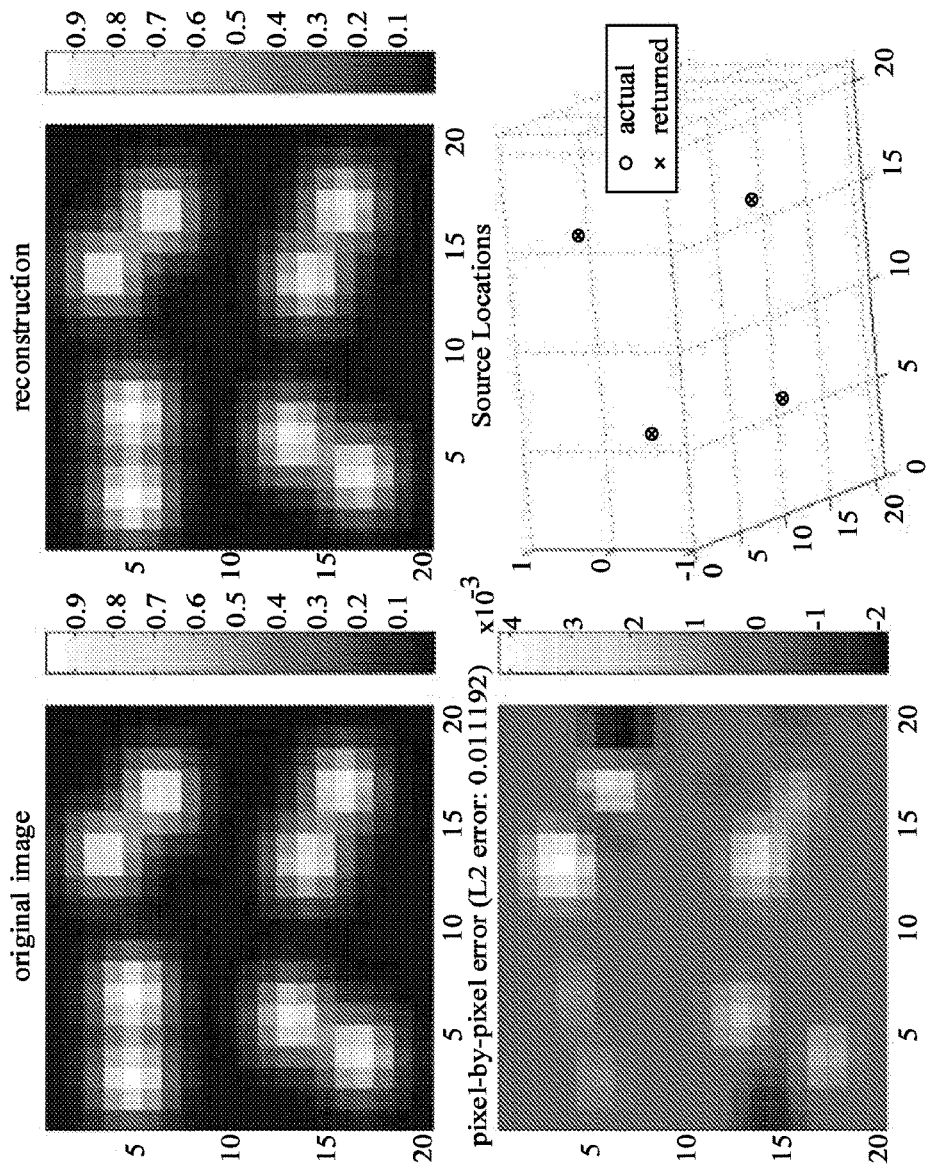
FIG. 17 illustrates an example of double-helix point spread function super-localization results according to some embodiments described herein.
Figure 18:
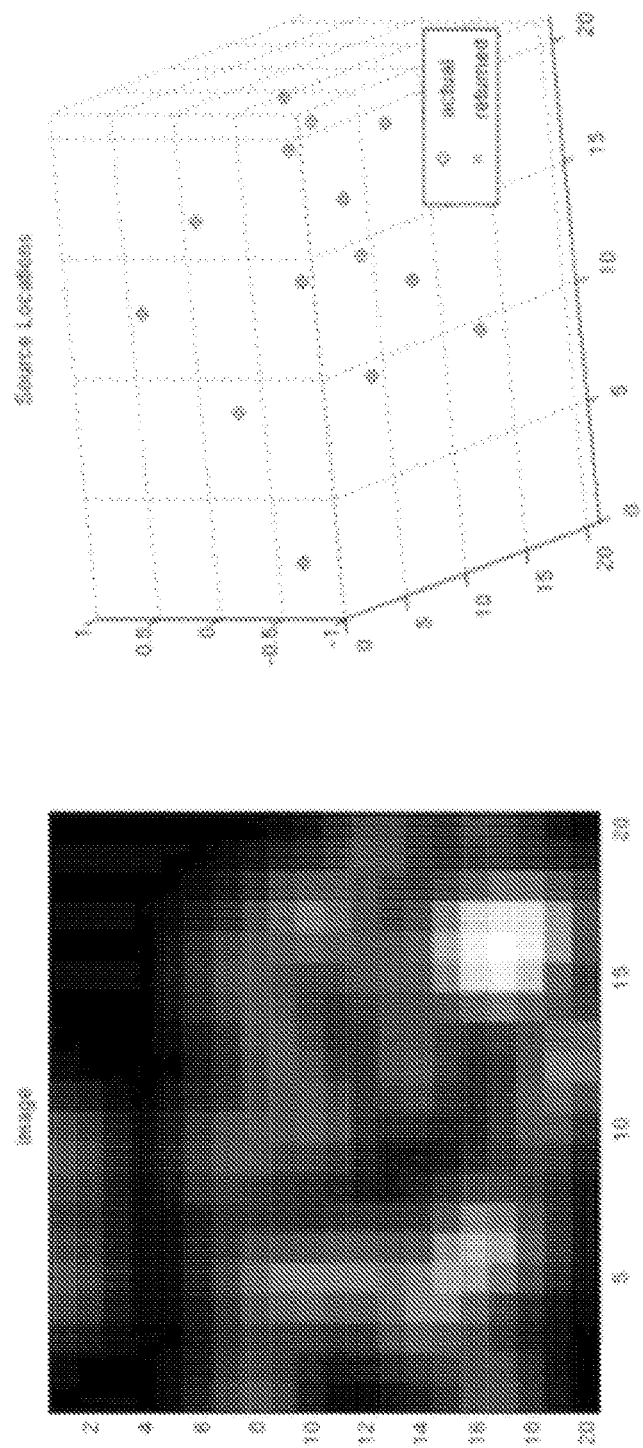
FIG. 18 illustrates an example of double-helix point spread function super-resolution results according to some embodiments described herein.

At block 515 a point spread function dictionary may be created having a number of different entries where each entry corresponds with the point spread function for a particle at different locations. The point spread function dictionary can be created from the model created in block 510. Each point spread function dictionary element may include a 2-D cross section of the point spread function corresponding to a different discrete particle location in a full 3-D space. Each point spread function dictionary element may correlate a point spread function response Examples of a point spread function dictionary are illustrated in FIG. 12 and FIG. 13, and are described in more detail below.

The step size between adjacent elements within a point spread function dictionary, in some embodiments, may be an important consideration. In some embodiments where localization precision is important, small steps may be used. In some embodiments where computational efficiency is important, large steps may be used. In some embodiments, steps having sub-pixel resolution may be used. In some embodiments, the point spread function dictionary may extend further in one direction than another. In some embodiments, the dictionaries may be over complete, meaning there are more elements in the point spread function dictionary then there are in pixels being imaged (D>N).

In some embodiments, block 505 and block 510 may be performed together. In some embodiments, block 510 and block 515 may occur during calibration, during setup, during development, and/or during manufacturing.

At block 520, coefficients of the point spread function dictionary elements that best represent the data may be estimated. Any number of techniques may be used to estimate these coefficients such as matching techniques, optimization techniques, fitting techniques, etc. These techniques may include, for example, a Matching Pursuit technique and/or a Convex Optimization technique. Other techniques may use the maximum-posterior estimator, maximum entropy, minimum discrimination, least squares, linear programming, convex quadratic minimization with or without linear constraints, quadratically constrained Convex-quadratic minimization with or without convex quadratic constraints, conic optimization, geometric programming, second order cone programming, semidefinite programming, Bayesian estimation, generalized Bayesian estimation, empirical Bayesian estimation, or recursive Bayesian estimation, and/or entropy maximization. In some embodiments, a combination of different techniques may be used. Moreover, in some embodiments, the estimation may be fully parametric, semi-parametric, and/or non-parametric. In some embodiments, the estimation may include information theoretic statistical inference, such as minimum description length.

At block 525, the number of particles may be determined from the point spread function dictionary coefficients. The estimates found in block 520 may be used to determine the number of particles that are present in the image. For instance, the estimates provided in block 520 may determine point spread function dictionary elements that are local or global maxima or minima. The number of these point spread function dictionary elements may correspond with the number of particles (or elements) in the image.

At block 525 the locations of the particles may be determined from the point spread function dictionary coefficients. Each point spread function dictionary element corresponds with a particle location in three-dimensional space. Thus, once the point spread function dictionary elements having local or global maxima or minima are identified, the location of the particles can be determined.

Figure 6:
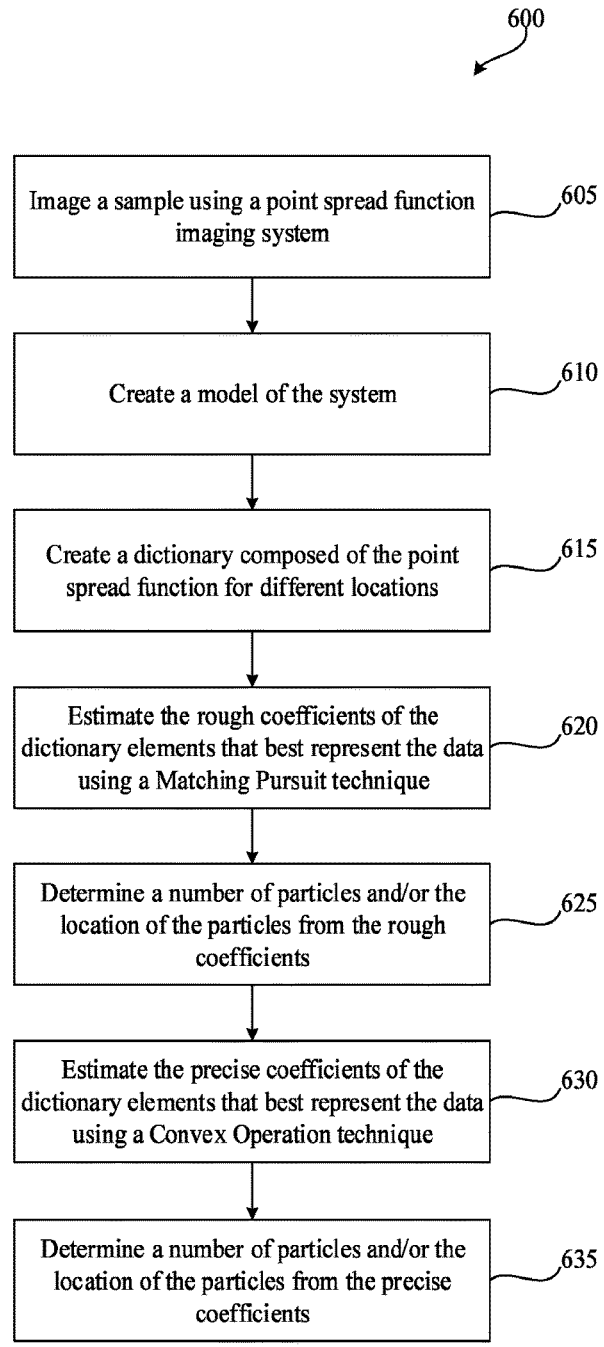
FIG. 6 is a flowchart of a process for determining the location of particles within a scene according to some embodiments described herein.

FIG. 6 is a flowchart of a process 600 for determining the location of particles within a scene according to some embodiments described herein. The process 600 uses two different techniques using dictionaries having different resolution (or fineness). The process 600 starts at block 605, which is similar to block 505 described above. Block 610 is similar to block 510 and block 615 is similar to block 515.

At block 620, rough coefficients of the point spread function dictionary elements that best represent the data can be estimated using a first technique such as, for example, the Matching Pursuit technique. The Matching Pursuit technique, for example, can use a coarse point spread function dictionary. A coarse point spread function dictionary, for example, may include fewer point spread function dictionary elements than the number of particles in the image.

At block 625, the rough number of particles and/or the rough location of the particles can be estimated from the rough coefficients determined above.

At block 630, from the rough number of particles and/or the rough location of the particles, the Convex Optimization technique may be used in the area around the rough locations of the particles. The Convex Optimization technique may use, for example, an over-complete point spread function dictionary that includes more point spread function dictionary elements than pixels in the image.

Processes 500 and/or 600 may be repeated any number of times using imaging subsystems having different point spread functions and different point spread function dictionaries. A number of different images may be returned. In some embodiments, these images may be statistically or mathematically combined to create a single image prior to determining the number and/or location of particles. In some embodiments, the number and/or location of particles in each image may be determined for each image and the average (or another function) location and/or number of particles may be determined. A first example of an iterative process for finding the locations of a number of sources is shown in FIGS. 7A-7F. In particular, the figures show an iterative process for finding the locations of five (5) sources.

Figure 7A:
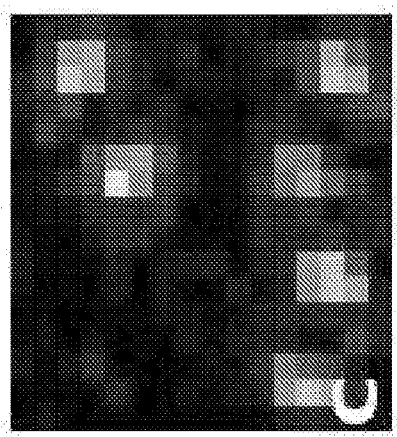
FIGS. 7A-7F illustrate a first example of an iterative process for finding the locations of a number of sources according to some embodiments described herein.
Figure 7B:
Figure 7C:
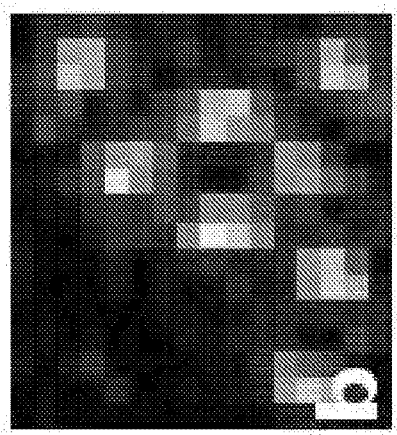
Figure 7D:
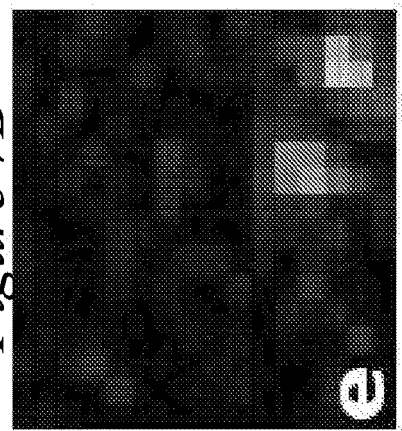
Figure 7E:
Figure 7F:
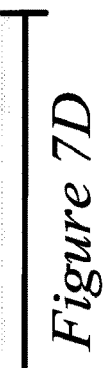

The original image is shown in FIG. 7A. FIG. 7B shows the remaining image after a first particle has been removed, and FIGS. 7C-7F show progressively fewer particles, as the locations' different particles are discovered and their point spread function is removed. The example simulation shown in FIGS. 7A-7F was performed using a double-helix point spread function, which encodes the axial location of the point source as a rotation of the dual lobes of the point spread function. Thus, the 3-D location of each particle is obtained as a result of the process.

Figures 8A, 8B:
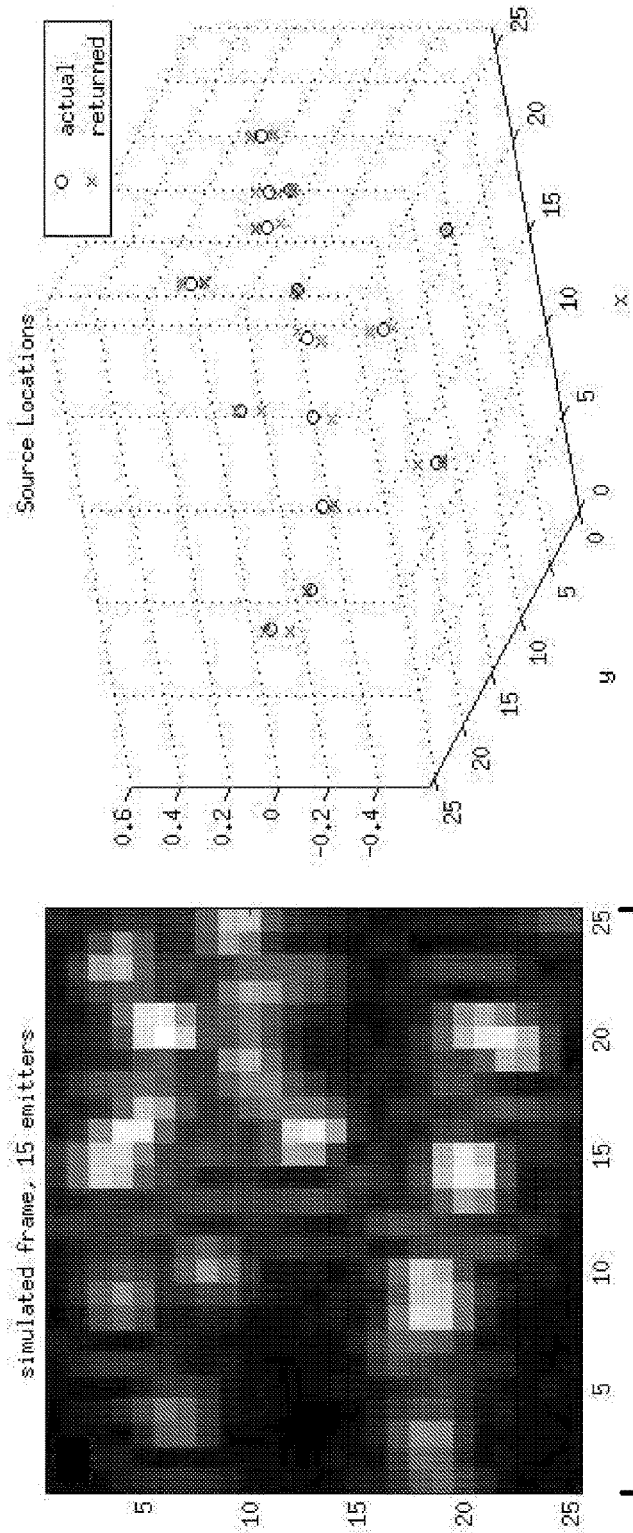
FIGS. 8A and 8B illustrate a second example of an iterative process for finding the locations of a number of sources according to some embodiments described herein.

FIGS. 8A and 8B show another example of an iterative process for finding the locations of a number of sources according to some embodiments described herein. FIG. 8A shows the original image. FIG. 8A is different than FIG. 7A in that the density of particles or sources is greater in FIG. 8A than in FIG. 7A. FIG. 8A illustrates the capability of the embodiments described herein to handle "dense" scenes. In FIG. 8A a simulated frame of many overlapping particles with double-helix point spread functions, and FIG. 8B shows the true (actual; shown as circles) and reconstructed (returned; shown as Xs) locations.

In this example, the simulation parameters were defined to be comparable to "typical" experimental conditions: emission wavelength 660 nm; imaging system NA 1.45; magnification 100×. These simulation parameters are similar to those used for the first example shown in FIGS. 7A-7F. By successfully localizing more particles in a dense scene, the data collection time can be significantly reduced. This is one example advantage and/or benefit of the systems, devices, and methods for resolving the number of particles within a scene in accordance with the present disclosure.

In some embodiments, the computational effort of performing the localization may be far less than in other methods, yielding faster processing times. The algorithm may be efficient and robust such that it may be implemented in hardware, allowing for the possibility of real-time super-resolution reconstructions at video rates. A further advantage of the systems, devices, and methods may be that background noise in the data is not reconstructed using the point spread function dictionary; the reconstruction produced is "noiseless" (see e.g., FIG. 7F).

With respect to the CO technique, rather than decomposing the data by iteratively choosing the set of coefficients to describe the scene, CO may arrive at an "optimal" and/or "approximate" representation of the image by solving for all the coefficients in parallel. This is possible by enforcing the assumption that the image is sparse in "point spread function space." This means that although the image may be defined as a large set of pixel values, it can be efficiently expressed as a much smaller number of coefficients that correspond to point spread functions. In the example of FIG. 8A, the image contains 25×25=625 pixel values, where each pixel corresponds to 160 nm (the other figures shown herein may be assumed to have the same resolution) but the sparse representation of the image is just 15 coefficients corresponding to the 15 sources in the scene. The sparsity assumption may allow the CO technique to discover the source locations in the scene.

The CO technique is conceptually similar to the MP technique. Although CO may have the potential to find a more optimal, and thus more correct, decomposition of the true image, this, however, may come with a computational cost. For this reason, it may be inadvisable to use CO on "standard" data sets. However, CO may be optimally used in performing the localization of data collected in a compressive manner. By combining the collection efficiency of compressive sensing with the methods, of the present disclosure, ability to handle high-density scenes, total observation times for a particular set of data may be reduced substantially or drastically.

As mentioned above, the sparsity assumption may allow embodiments described herein such as, for example, the CO technique, to discover the source locations in an image. In particular, the sparsity assumption when used in combination with compressive sensing (CS) may yield localization and super-resolution results. Simulations indicate this point spread function dictionary may be employed to achieve arbitrary localization precision. When used in combination with a microscope equipped with a point spread function (e.g., as shown in FIG. 3) such as, for example, a double-helix point spread function or a lateral point spread function, 3-D super-resolution is achievable.

In some embodiments described herein, a signal may be recovered using far fewer measurements than Shannon's sampling theory predicts. This may allow for stable reconstruction of large signals using "small" numbers of measurements.

Embodiments described herein may include a transform from "image space" to "measurement space." This may be written mathematically as $$M = CS \times I \qquad \text{equation 1}$$

sizes: $[K \times 1] = [K \times N] \times [N \times 1]$.

I is the image expressed as a column vector, CS is the measurement matrix, and M is the vector containing the set of K measurement values.

For an image with N pixels resulting from an s-sparse signal (a signal that can be represented by s non-zero coefficients in some basis), the number of required samples for stable recovery is:

$$K = s \log N/s. \quad \text{equation 2}$$

The matrix CS may spread some information about the coefficients of the underlying signal into many measurements. For this reason, the measurement matrix may be populated with random values from a Gaussian distribution or a set of random 1 s and 0 s.

To reconstruct the image from the measurements, another transform may be introduced. This is the transform from "sparse space," also referred to as "feature space," to image space. Here, M may be re-written as:

$$M = CS \times T \times \chi, \quad \text{equation 3}$$

$[K \times 1] = [K \times N] \times [N \times N] \times [N \times 1]$.

T is a matrix representing the image transform, and x is the s-sparse vector containing the coefficients that describe the image I. Further, T is a square matrix, and may represent any signal decomposition, such as a Fourier basis or a wavelet basis. Given this assumption about the vector $\chi$, the reconstruction problem may be formulated as convex optimization. An algorithm is written to maximize the sparsity of x while enforcing that the measurements are accurate; in mathematical terms:

$$\min \|\tilde{x}\|_1 \quad \text{equation 4}$$
$$\text{subject to } \|M - \overline{CS \times} T \times \tilde{x}\|_2 \leq \varepsilon,$$

$\tilde{\chi}$ is the variable that is being solved for, and $\epsilon$ is the $l_2$ error threshold at which it will be decided that a solution has been found (in the absence of noise, $\epsilon = 0$).

An image transform may be selected to perform feature-extraction on an image such as, for example, an image made from fluorescence microscopy data, in accordance with some embodiments described herein. In general, in some embodiments the goal of fluorescence microscopy may be to accurately and/or precisely determine the location of particles within the volume of a sample. By selecting an image transform that goes from feature space to image space, an algorithm (e.g., a CS algorithm) may be used to solve for the desired measurements. When using an imaging system with the capability of producing a #-D point spread function (e.g., a 3-D point spread function) such as the double-helix point spread function or the lateral point spread function, this idea may be extended to 3-D super-resolution.

In some embodiments, the basis set for the CS recovery algorithm may be selected to take advantage of all possible assumptions. And, in some embodiments the basis may not form an orthonormal set. There is freedom in selecting a basis set, because any restrictions imposed by the recovery scheme may apply to the product of the random measurement matrix and the basis set. The basis set, for example, may be chosen to obey the Restricted Isometry Property (RIP), shown below as:

$$(1-\delta_s)\|\chi\|_2^2 \leq \|A\chi\|_2^2 \leq (1-\delta_s)\|\chi\|_2^2 \quad \text{equation 5}$$

The main implication of this property is that each subset of s rows from the full set of K total rows approximate an orthonormal set.

In fluorescence microscopy experiments, in which the goal is to determine the location of particles in a sample, the images consist of a sparse set of images of the systems point spread function. Thus, it is contemplated that a choice of basis elements would be images of the system point spread function shifted to different locations in the field of view. Smaller shifts in the point spread function may result in more precise localization results. However, this increased precision may come with a cost of increased computational complexity and a less strict adherence to the RIP. An example of the basis elements of images of the system point spread function is shown in FIG. 12 and FIG. 13.

Figure 9B:
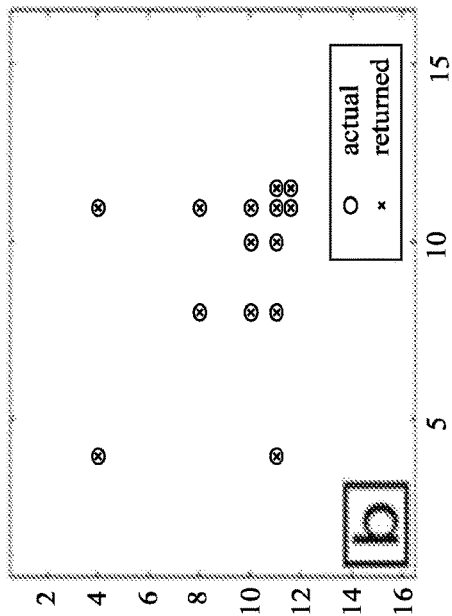
FIGS. 9A and 9B illustrate simulation results demonstrating super-resolution and localization using a point spread function basis according to some embodiments described herein.
Figure 9A:
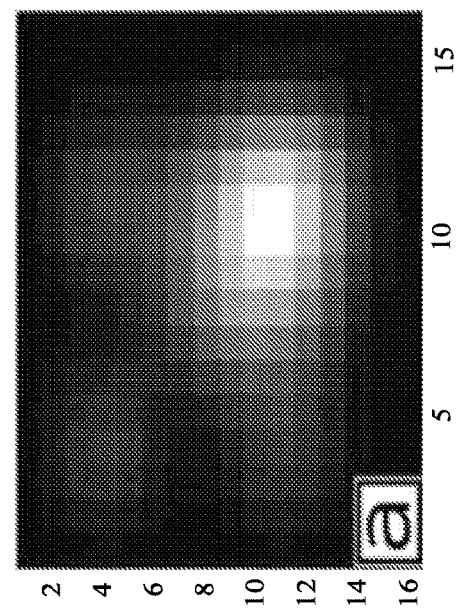

FIG. 9A and FIG. 9B show results demonstrating super-resolution and localization using a point spread function basis. FIG. 9A shows the image; and FIG. 9B shows the reconstructed particle locations. In this example, particles are separated by 4, 2, 1, and 0.5-pixel increments. The point spread functions are 4 pixels wide, so these particles are located much closer than the resolution limit declared by Ernst Abbe (resolution limit is proportional to the wavelength, and inversely proportional to numerical aperture). The group of 4 sources in the bottom right of FIG. 9B is separated by ⅛th of a spot size; for a high-numerical aperture system, this corresponds to a separation on the order of approximately or about 20 nm, which is about the size of a quantum dot. By exploiting the sparsity assumption, embodiments described herein using, for example, compressive sensing, may accurately resolve and/or localize these closely-spaced particles using significantly fewer measurements.

As mentioned above in connection with FIG. 7, the double-helix point spread function encodes the axial location of the point source as a rotation of the dual lobes of the point spread function. And the lateral point spread function encodes the axial location of the point source as a lateral distance between two lobes or as a lateral distance of one or more of two lobes from a roughly orthogonal axis. In some embodiments, these point spread functions may be used in combination with CS. For instance, a CS algorithm may be modified to account for all shifts of the source throughout the 3-D volume, rather than just the transverse space. Although this may force the point spread function dictionary to be "over-complete," the algorithm may still find solutions. The difficulty in finding a solution may be eased by including more measurements than equation 2 dictates.

Referring now back to FIG. 8A and FIG. 8B, which shows simulation results for a "dense" volume containing 15 sources. The image in FIG. 8A may be difficult to interpret visually. However, using only 1.4 times the number of measurements dictated by equation 2, the algorithm of the present disclosure may accurately localize all 15 particles in the volume.

FIGS. 10-18 illustrate in further detail CS and 3-D super-resolution in fluorescence microscopy in accordance with the present disclosure.

Figure 10:
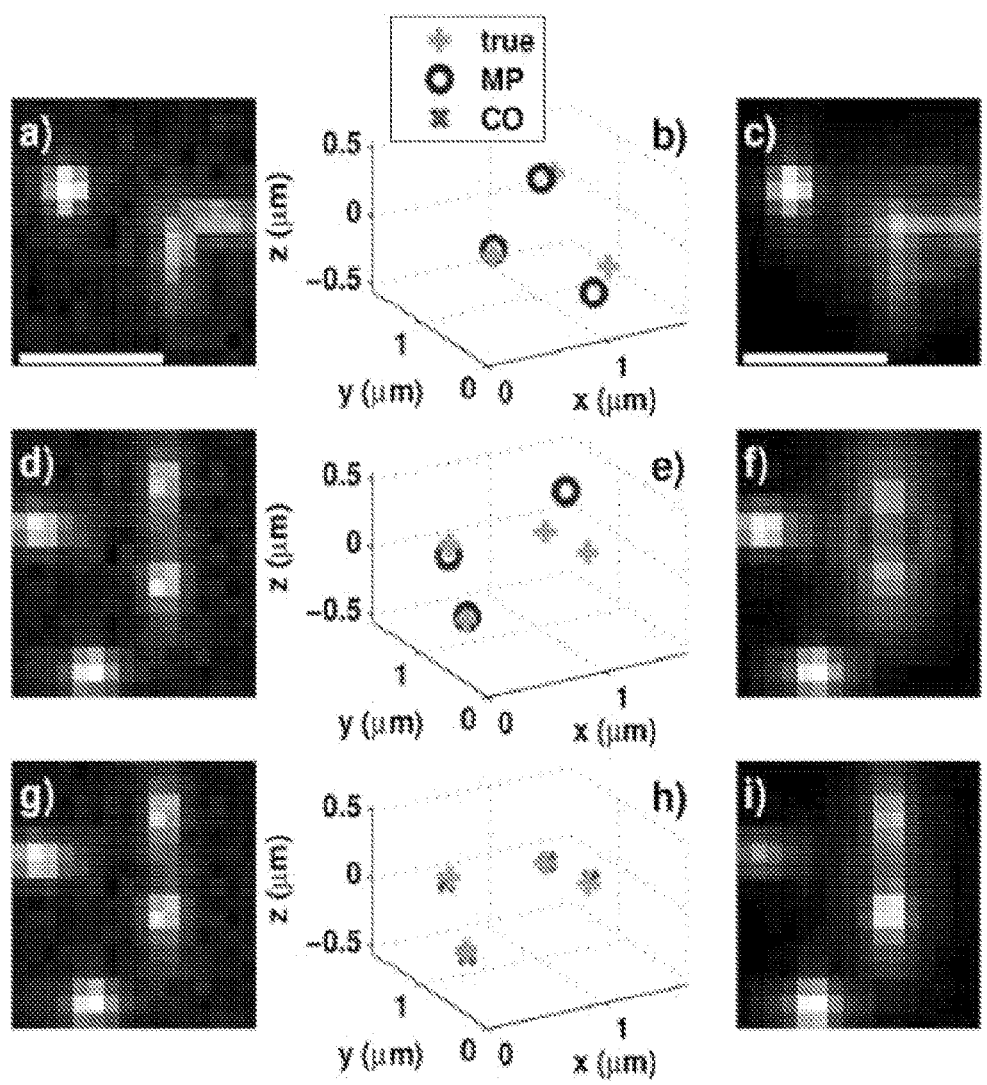
FIG. 10 illustrates a demonstration of 3D super-resolution and super-localization with an Astigmatic point spread function according to some embodiments described herein.

FIG. 10 illustrates a demonstration of 3D super-resolution and super-localization with an Astigmatic point spread function according to some embodiments described herein. The top row shows a successful localization of overlapping particles using MP. The simulated frame is shown in a), the true and returned locations are in b), and the reconstructed image is in c). The second row demonstrates a common problem encountered in simulations with closely-spaced astigmatic point spread functions. Here, two in-focus point spread functions are incorrectly grouped into one defocused (elongated) point spread function. However, this problem was not encountered when using CO, as seen in the localizations in g) and the reconstructed image in h). In all images, scale bars are 1 m (scale bars omitted in d-i to avoid interfering with the image, but the scaling may be the same as in a,c).

Figures 11A, 11B, 11C, 11D, 11E, 11F:
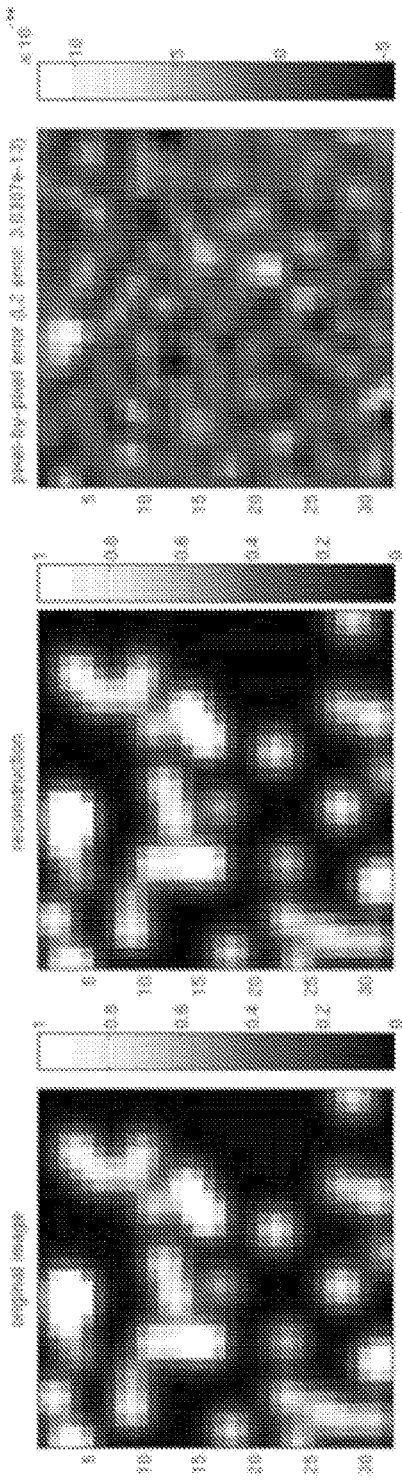
FIGS. 11A-11F illustrate a first example simulation summary of the example reconstruction technique of FIG. 10 according to some embodiments described herein.

FIG. 11A illustrates an example of an original image that was imaged using a point spread function. This image could be imaged, for example, using an optical system such as the one shown in FIG. 3. The image may be an image of the particles shown in FIG. 11D.

FIG. 11B shows the reconstructed image. The reconstructed image can be reconstructed using a point spread function dictionary such as, for example, the point spread function dictionaries shown in FIG. 12 and FIG. 13. The reconstructed image may also be reconstructed using the process 500 and/or the process 600. FIG. 11D illustrates the particles that can be found in the image shown in FIG. 11A using embodiments described herein.

In general, FIGS. 7-11 demonstrate the ability of the techniques of the present disclosure to resolve and localize dense sets of particles from a limited number of measurements. In some embodiments, the sample is assumed to contain a mathematically sparse set of sources, and the "point spread function dictionary" of the present disclosure is a "highly" efficient expression of the scene.

FIGS. 12-18 illustrate 3-D super-resolution in the context of CS in accordance with the present disclosure. In particular, an example 2-D point spread function dictionary, with x-y representation, for localization with arbitrary precision, may be visualized with reference to FIG. 12. An example 3-D point spread function dictionary, with x-z representation, for localization with arbitrary precision, may be visualized with reference to FIG. 13. An example of "standard" localization results may be visualized with reference to FIG. 14. An example of super-localization results may be visualized with reference to FIG. 15. An example of super-resolution results may be visualized with reference to FIG. 16. An example of double helix point spread function super-localization results may be visualized with reference to FIG. 17. An example of double helix point spread function super-resolution results may be visualized with reference to FIG. 18. In general, FIGS. 12-18 demonstrate some examples of potential applications of the concept of the "highly" efficient "dictionaries" of the present disclosure. When the data are known to consist of a limited set of patterns, a reconstruction of the data using such a point spread function dictionary can very efficiently represent the desired information hidden in the data. This enables such methods to perform well even under non-ideal situations such as high noise, low signal, reduced numbers of measurements, dense scenes, and high-dimensional data. Still other advantages are possible as well.

In some embodiments a point spread function dictionary may include a 2D point spread function corresponding to lateral and/or axial shifted locations of the point source. If, for example, the system is shift-invariant for a given depth, all 2D point spread functions may be equal except for a transverse shift. The dictionary entries may be generated by first selecting a 3D window size and making a list of discrete 3D locations to fill this volume. A model is then used to generate the corresponding image for each point source location in the dictionary. The model may be either an ideal point spread function, or it may be the result of calibration data from the specific imaging system. The step size of the locations in the dictionary may be used to determine the localization precision. Thus, in some embodiments, the step size may be very fine. In some embodiments, the step size may be related to the limit of localization precision achievable in a given system, as calculated by the Cramer-Rao Lower Bound (CRLB). In some embodiments, the effective pixel size (physical pixel size divided by magnification) in single-particle detection systems may be designed to sample the point spread function at approximately Nyquist sampling, which may result in effective pixel sizes on the order of, for example, 160 nm. The CRLB, on the other hand, can be significantly lower (typically 10 to 20 nm). As a result, the dictionary may result in sub-pixel shifts. Additionally, since the extent of the point spread function is significantly larger than the step size, there may be a high degree of similarity between adjacent dictionary elements. Hence, by definition, the dictionary may be coherent.

Furthermore, the requirement for 3D information may result in many dictionary elements at the same transverse location. In some embodiments, the point spread function (e.g., the double helix point spread function) may enable an extended depth of field (DOF) as compared to a standard aperture by approximately a factor of two. In some embodiments a 1.45 NA objective may be used with a DOF of approximately 2_m. However, since the CRLB is larger in the axial dimension than in the transverse dimensions, the axial step size can be also slightly larger than the transverse step size.

Because the dictionary contains discrete locations, the results may have a quantization error. Even if the localization algorithm returns the correct dictionary element for every particle in a scene, there will still be a distribution of errors spanning a range between $-d/2$ to $+d/2$, where d is the step size. The standard deviation of a uniform distribution with a range of d is $d/\sqrt{12}$. The standard deviation may be chosen to characterize the error because it can be directly compared to the CRLB, which can be stated as a standard deviation. In some embodiments, the standard deviation may be used to quantify the magnitude of the error in simulations.

In some embodiments, the goal is not to generate a reconstruction of each image. Although a reconstruction image may be obtained, the desired information may be actually in the indices of the large coefficients in the sparse reconstruction. Each dictionary element may have a physical meaning: the presence of a large coefficient in the solution means there is a particle at the corresponding location. To keep track of this, each dictionary may carry with it a LUT to convert the index of a dictionary element to a physical location. The LUT is a D-by-3 matrix, where D is the number of dictionary elements. There are three columns because the solution space is 3D. Each row contains the (x,y,z) values describing the location of a particle 8 that would generate the point spread function in the corresponding index of the dictionary. The LUT may be easily generated alongside the dictionary, and may provide a simple way to obtain a physical interpretation of the coefficients in the solution.

Each element of the dictionary may be normalized such that its L2 norm is unity. When this is the case, the product of the coefficient and the dictionary element may match the intensity of that component in the image. The corresponding number of photons may be calculated by multiplying the coefficient with the L1 norm of that particular basis element. This is only true, of course, if the data has previously been converted from camera counts to photons. A matrix containing the L1 norms for each dictionary element may be calculated beforehand and stored with the dictionary for fast conversion from coefficient values to photon counts. It may be necessary to calculate photon counts frequently, since one of the stopping criteria for the iterative method requires knowledge of the number of photons.

In some embodiments, the coefficients for representing the image could be found by the inner product of the image and each individual dictionary element. The use of small sub-pixel shifts means adjacent dictionary elements have a high degree of similarity; they cannot be orthonormal. Therefore, the coefficients may be found using Matching Pursuit (MP) and Convex Optimization (CO).

MP is similar to finding coefficients for an orthonormal dictionary. In one iteration of MP the image may be projected onto the dictionary, just as if the dictionary were orthonormal. However, instead of keeping all the resulting coefficients, only the largest coefficient is stored as part of the solution. Next, that element is subtracted from the image. Iterations may continue until a stopping criterion is met.

Implementation of the Matching Pursuit (MP) algorithm may use any type of stopping criteria. One stopping criterion, for example, may limit the number of iterations (i.e. the maximum number of particles the algorithm will return for a given scene). Simulations indicate the reliability of the algorithms decreases as the particle density increases. Therefore results that are likely to be erroneous may not be recorded. Not only is a limit placed on the maximum iterations, but the order in which results are subtracted from the scene is also recorded. With this information, the performance of the iterative algorithm may be observed as the density increases in an experimental setting.

Another stopping criterion, for example, may be the minimum estimated number of photons from a particle. Even when all the particles in a scene have been accounted for and subtracted, the remainder will still have positive values due to noise (particularly background noise). This could lead to spurious particles in the reconstruction. To avoid this, MP ends iterations if the photon count of the strongest remaining component is below a threshold. This threshold can be determined beforehand based on the particles used in the experiment, or the threshold can be decided afterwards based on the data set. In this second case, a preliminary threshold must be set to a very low value. Once MP is complete, the threshold can be raised and the weakest particles are excluded from the results.

Another stopping criterion, for example, may involve placing a limit on the value of pixels in the remainder image. As above, when all actual particles in a scene are accounted for and subtracted, there will still be a remainder due to noise. Once the maximum pixel value in the remainder image drops below the expected value of background in the data set, the subsequent localizations are likely a result of noise only. Therefore, the iterations are stopped when the maximum of the remainder image drops below a threshold. Typical background levels can be predicted accurately from examining statistics of the whole data set. Furthermore, this criterion is usually set slightly below the background level (by perhaps 75%) to avoid false negatives.

Many other embodiments of MP (or other iterative algorithms) may employ a stopping criterion that compares the reconstructed image to the raw data. Iterations stop when the error between the two has reached an acceptable level. In some embodiments, a limit on the error between the reconstruction and the original data would be meaningless in the case of a scene that contains no particles.

Estimation using CO, on the other hand, may attempt to arrive at a solution for the significant coefficients in parallel. Although the estimation method is quite different, the use of the algorithm is similar with the inputs are a window of data and a dictionary, and the output is a list of coefficients that describe the data. The reconstruction problem may be formulated as a convex problem in which the variable to be optimized is the sparsity of the coefficient vector (quantified as the L1 norm). This can be phrased mathematically as:

$$\text{minimize} \|x\|_1 \text{ subject to } \|Ax-b\|_2 \leq \epsilon,$$

where x is the set of coefficients, A is the dictionary, and $\epsilon$ is an error bound related to the total intensity in the image. In this formalism, the image b has been folded into a column vector.

In some embodiments, the set or a set of coefficients of the "point spread function dictionary" of the present disclosure may be found based on a number of various criteria that may or may not include other prior information about the scene or the imaging system. For instance, one class of optimality criteria is the class of information theoretic criteria, which are based on a probabilistic formulation of the problem. One particular example is the maximum-likelihood principle for estimation of a set of parameters (the coefficients in this case). Other examples are the maximum-posterior estimator principle, maximum entropy, or minimum discrimination principles. Other estimators may also be used.

Figure 19:
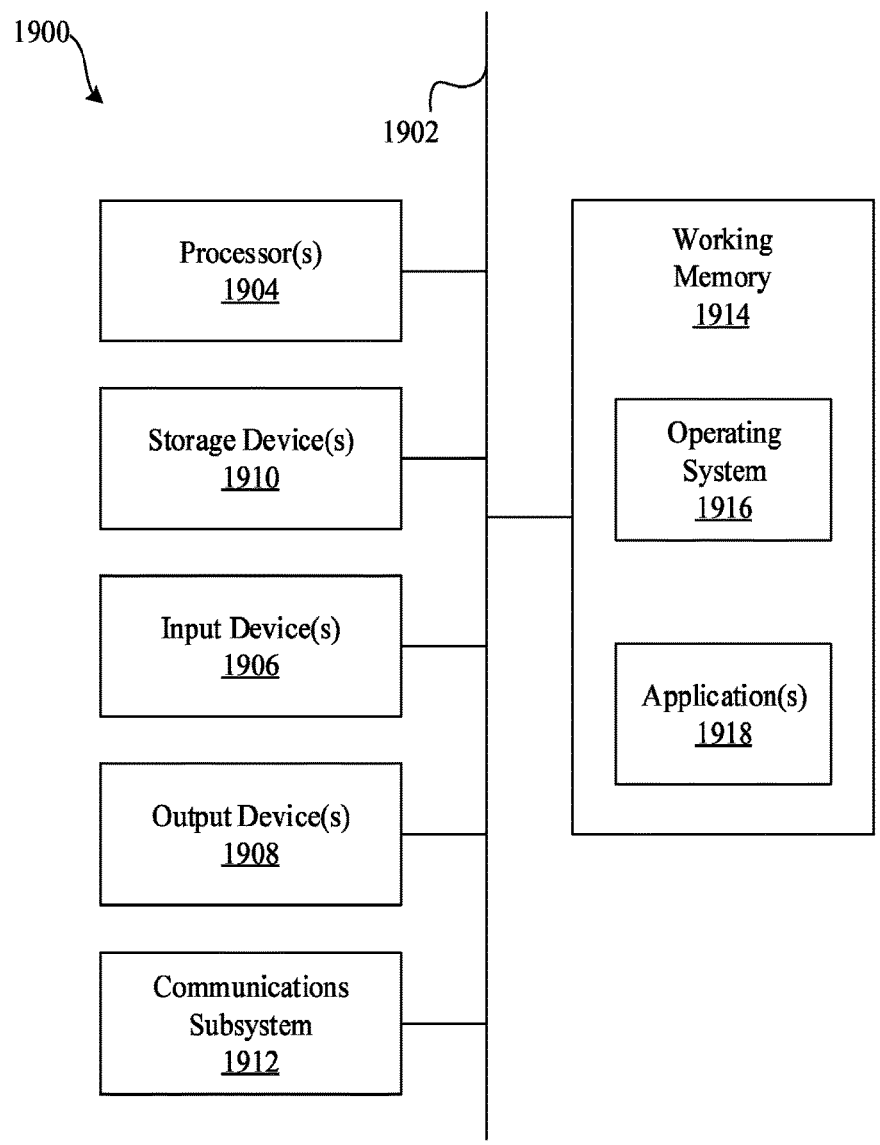
FIG. 19 shows an example computing system or device according to some embodiments described herein.

FIG. 19 shows an embodiment of an example computer system or device 1900 in accordance with the present disclosure. An example of a computer system or device includes a desktop computer, laptop computer, smartphone, and any other type machine configured for performing calculations. In particular, the example computer device 1900 may be configured to implement various measurement techniques and processing algorithms described in accordance with the present disclosure. Computer system 1900 may be part of a parallel computation system such as, for example, a GPU. Various processes, equations, calculations, etc. may be performed in parallel.

For example, as shown in FIG. 2000, multiple optical subsystems may be used that returns multiple images produced from these multiple optical subsystems. Processes described herein may operate on each image using different parallel computation systems. Various other parallel processing configurations may be implemented.

The computer device 1900 is shown comprising hardware elements that may be electrically coupled via a bus 1902 (or may otherwise be in communication, as appropriate). The hardware elements may include a processing unit with one or more processors 1904, including, without limitation, one or more general-purpose processors and/or one or more special-purpose processors (such as digital signal processing chips, graphics acceleration processors, and/or the like); one or more input devices 1906, which can include, without limitation, a remote control, a mouse, a keyboard, and/or the like; and one or more output devices 1908, which can include, without limitation, a presentation device (e.g., television), a printer, and/or the like.

The computer device 1900 may further include (and/or be in communication with) one or more non-transitory storage devices 1910, which can comprise, without limitation, local and/or network accessible storage, and/or can include, without limitation, a disk drive, a drive array, an optical storage device, a solid-state storage device, such as a random access memory, and/or a read-only memory, which can be programmable, flash-updateable, and/or the like. Such storage devices may be configured to implement any appropriate data stores, including, without limitation, various file systems, database structures, and/or the like.

The computer device 1900 might also include a communications subsystem 1912, which can include, without limitation, a modem, a network card (wireless or wired), an infrared communication device, a wireless communication device, and/or a chipset (such as a Bluetooth™) device, an 802.11 device, a WiFi device, a WiMax device, cellular communication facilities (e.g., GSM, WCDMA, LTE, etc.), and/or the like. The communications subsystem 1912 may permit data to be exchanged with a network (such as the network described below, to name one example), other computer systems, and/or any other devices described herein. In many embodiments, the computer device 1900 will further comprise a working memory 1914, which may include a random access memory and/or a read-only memory device, as described above.

The computer device 1900 also can comprise software elements, shown as being currently located within the working memory 1914, including an operating system 1916, device drivers, executable libraries, and/or other code, such as one or more application programs 1918, which may comprise computer programs provided by various embodiments, and/or may be designed to implement methods, and/or configure systems, provided by other embodiments, as described herein. By way of example, one or more procedures described with respect to the method(s) discussed above, and/or system components might be implemented as code and/or instructions executable by a computer (and/or a processor within a computer); in an aspect, then, such code and/or instructions can be used to configure and/or adapt a general-purpose computer (or other device) to perform one or more operations in accordance with the described methods.

A set of these instructions and/or code might be stored on a non-transitory computer-readable storage medium, such as the storage device(s) 1910 described above. In some cases, the storage medium might be incorporated within a computer system, such as the computer device 1900. In other embodiments, the storage medium might be separate from a computer system (e.g., a removable medium, such as flash memory), and/or provided in an installation package, such that the storage medium can be used to program, configure, and/or adapt a general-purpose computer with the instructions/code stored thereon. These instructions might take the form of executable code, which is executable by the computer device 1900 and/or might take the form of source and/or installable code, which, upon compilation and/or installation on the computer device 1900 (e.g., using any of a variety of generally available compilers, installation programs, compression/decompression utilities, etc.), then takes the form of executable code.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer system (such as the computer device 1900) to perform methods in accordance with various embodiments described herein. According to a set of embodiments, some or all of the procedures of such methods are performed by the computer device 1900 in response to the processor(s) 1904 executing one or more sequences of one or more instructions (which might be incorporated into the operating system 1916 and/or other code, such as the application program 1918) contained in the working memory 1914. Such instructions may be read into the working memory 1914 from another computer-readable medium, such as one or more of the storage device(s) 1910. Merely by way of example, execution of the sequences of instructions contained in the working memory 1914 may cause the processor(s) 1904 to perform one or more procedures of the methods described herein.

The terms "machine-readable medium" and "computer-readable medium," as used herein, may refer to any medium that participates in providing data that causes a machine to operate in a specific fashion. In an embodiment implemented using the computer device 1900, various computer-readable media might be involved in providing instructions/code to the processor(s) 1904 for execution and/or might be used to store and/or carry such instructions/code. In many implementations, a computer-readable medium is a physical and/or tangible storage medium. Such a medium may take the form of a non-volatile media or volatile media. Non-volatile media may include, for example, optical and/or magnetic disks, such as the storage device(s) 1910. Volatile media may include, without limitation, dynamic memory, such as the working memory 1914.

Example forms of physical and/or tangible computer-readable media may include a floppy disk, a flexible disk, hard disk, magnetic tape, or any other magnetic medium, a CD-ROM, any other optical medium, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 1904 for execution. By way of example, the instructions may initially be carried on a magnetic disk and/or optical disc of a remote computer. A remote computer might load the instructions into its dynamic memory and send the instructions as signals over a transmission medium to be received and/or executed by the computer device 1900.

The communications subsystem 1912 (and/or components thereof) generally will receive signals, and the bus 1902 then might carry the signals (and/or the data, instructions, etc. carried by the signals) to the working memory 1914, from which the processor(s) 1904 retrieves and executes the instructions. The instructions received by the working memory 1914 may optionally be stored on the storage device(s) 1910 either before or after execution by the processor(s) 1904.

FIG. 20 illustrates an example imaging system process 2000 for imaging particles 2005 using a point spread function according to some embodiments described herein. Imaging system process 2000 may be used to produce N image frames 2015 of particles 2005 using optical systems 2010. Each optical system 2010 may a point spread function that may or may not be different than other point spread functions in other optical systems 2010. Each optical system 2010 may include all or portions of optical system 300 described in FIG. 3. The number and/or location of particles may be determined at 2020 using various embodiments described herein.

In one example, a first optical subsystem 2010-1 may include a double-helix point spread function and may produce image frame 2015-1. A second optical subsystem 2010-N may include a lateral point spread function and may produce image frame 2015-N. The number and/or location of the particles 2005 may be estimated from each image frame. The results of these two image frames may be combined (e.g., averaged, etc.) to estimate the number and/or location of the particles 2000. Any number of optical subsystems 2010 may be used with any number or combination of point spread functions.

Figure 21:
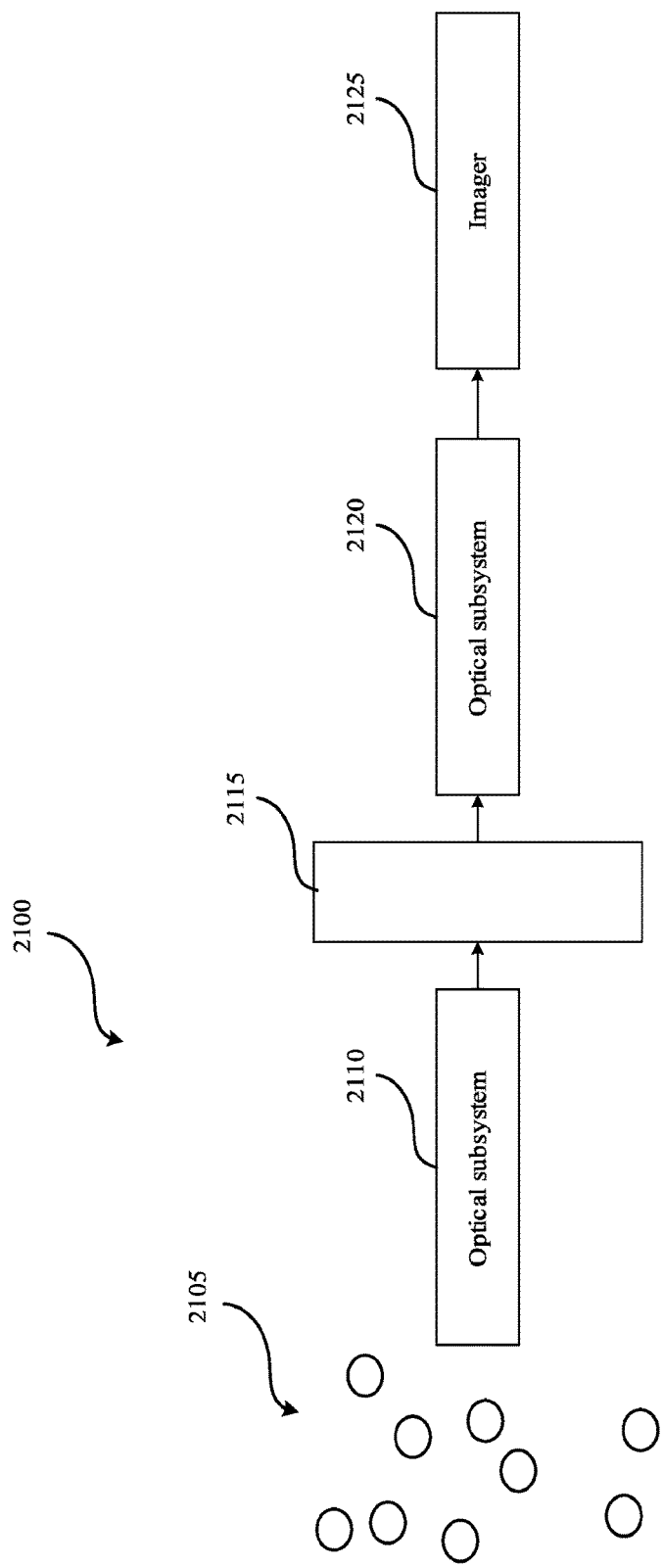
FIG. 21 illustrates an example imaging system process for imaging particles using a point spread function according to some embodiments described herein.

FIG. 21 illustrates an example imaging system 2100 for imaging particles 2005 using a point spread function according to some embodiments described herein. Imaging system 2105 may include optical subsystem 2110 and/or optical subsystem 2120. A mask 2015 may be placed between optical subsystem 2010 and optical subsystem 2120. The mask 2115 may be a reflective mask, a refractive mask, a diffractive element, a reflective element, a spatial light modulator, an amplitude mask, and/or a phase/amplitude mask, etc. A detector array 2125 may be used to collect images of the particles 2005 through the optical subsystems 2110 and/or 2120 and the mask 2115.

The methods, systems, and devices discussed above are examples. Various configurations may omit, substitute, or add various method steps or procedures, or system components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims. Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Furthermore, the example embodiments described herein may be implemented as logical operations in a computing device in a networked computing system environment. The logical operations may be implemented as: (i) a sequence of computer implemented instructions, steps, or program modules running on a computing device; and (ii) interconnected logic or hardware modules running within a computing device.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for detecting the number and/or location of particles, the method comprising:
    imaging a plurality of particles using an imaging system having a point spread function, wherein the imaging returns an image;
    estimating a plurality of point spread function dictionary coefficients of the image using a point spread function dictionary, wherein the point spread function dictionary includes a plurality of point spread function responses that each correspond with a different particle position; and
    determining the number and/or location of the particles in the image from the point spread function dictionary coefficients.

2. The method according to claim 1, further comprising:
    imaging the plurality of particles using a second imaging system having a second point spread function, wherein the imaging returns a second image;
    estimating a plurality of second point spread function dictionary coefficients of the image using a second point spread function dictionary, wherein the second point spread function dictionary includes a plurality of second point spread function responses that each correspond with a different particle position; and
    determining the number and/or location of the particles in the image from the second point spread function dictionary coefficients.

3. The method according to claim 1, further comprising determining the brightness of the particles in the image.

4. The method according to claim 1, wherein the point spread function changes as a function of the axial location of the plurality of particles.

5. The method according to claim 1, further comprising determining a two-dimensional location of each particle in the image from the point spread function dictionary coefficients.

6. The method according to claim 1, further comprising determining a three-dimensional location of the particles in the image from the point spread function dictionary coefficients.

7. The method according to claim 1, wherein the number of particles in the image is determined from a number of point spread function dictionary coefficients above or below a threshold value.

8. The method according to claim 1, wherein the point spread function dictionary comprises a plurality of point spread function responses that correspond with a plurality of three-dimensional spatial position of the particle.

9. The method according to claim 1, wherein the point spread function dictionary comprises a plurality of point spread function responses that correspond with a plurality of two-dimensional spatial position of the particle.

10. The method according to claim 1, wherein the point spread function comprises a double helix point spread function.

11. The method according to claim 1, wherein the point spread function comprises an astigmatic point spread function.

12. The method according to claim 1, wherein the point spread function produces lobes in the image that are displaced based on the axial position of the plurality of particles.

13. The method according to claim 1, wherein the plurality of coefficients of the image of the particles are estimated using either or both a Matching Pursuit algorithm and a Convex Optimization algorithm.

14. The method according to claim 1, wherein the plurality of coefficients of the image of the particles are estimated using an optimization algorithm.

15. An imaging system comprising:
a plurality of optical elements configured to image a plurality of objects, wherein the optical elements generate a point spread function, and wherein the point spread function changes as a function of the axial location of the plurality of objects;
an imager configured to image the plurality of objects located onto an image plane;
a memory including a point spread function dictionary that includes a plurality of point spread function responses that each correspond with a different position of an object; and
a processor configured to estimate a plurality of point spread function dictionary coefficients of an image of the plurality of objects using the point spread function dictionary and determine the number and/or position of objects in the image using the point spread function dictionary coefficients.

16. The system according to claim 15, wherein the processor is further configured to determine a two-dimensional location of the plurality of particles in the image from the point spread function dictionary coefficients.

17. The system according to claim 15, wherein the number of objects in the image is determined from a number of point spread function dictionary coefficients above or below a threshold value.

18. The system according to claim 15, wherein the point spread function produces lobes in the image that are displaced based on the axial position of the plurality of objects.

19. The system according to claim 15, wherein the point spread function dictionary comprises a plurality of point spread function responses that correspond with a three-dimensional spatial position of the objects.

20. The system according to claim 15, wherein the point spread function dictionary comprises a plurality of point spread function responses that correspond with a two-dimensional spatial position of the objects.

21. The system according to claim 15, wherein the plurality of point spread function dictionary coefficients of the image of the objects are estimated based on an optimization algorithm selected from the list consisting of Convex Optimization; Matching Pursuit; orthogonal Matching Pursuit; maximum likelihood estimation; Bayesian information criteria, maximum-likelihood principle; maximum-posterior estimator principle; maximum entropy principle; and minimum discrimination.

22. A method for detecting particles comprising:
imaging a plurality of particles using a first point spread function that changes as a function of the axial location of a particle, wherein the imaging returns an image;
estimating a first plurality of point spread function dictionary coefficients of the image using a Matching Pursuit algorithm with a point spread function dictionary that includes a plurality of point spread function responses corresponding to a different particle position;
determining a first region within which the particles are located in the image from the first plurality of point spread function dictionary coefficients;
estimating a second plurality of point spread function dictionary coefficients of the image using a Convex Optimization algorithm with a second point spread function dictionary that includes a plurality of point spread function responses corresponding to different particle position; and
determining a location of the particles in the image from the second plurality of coefficients.

23. The method according to claim 22, wherein the number of point spread function responses in the second point spread function dictionary is greater than the number of point spread function responses in the first point spread function dictionary.

24. The method according to claim 22, wherein the spatial resolution of the point spread function responses in the second point spread function dictionary is greater than the spatial resolution of the point spread function responses in the first point spread function dictionary.

* * * * *

UNITED STATES PATENT AND TRADEMARK OFFICE
CERTIFICATE OF CORRECTION

PATENT NO. : 9,858,464 B2
APPLICATION NO. : 14/777361
DATED : January 2, 2018
INVENTOR(S) : Piestun et al.

Page 1 of 1

It is certified that error appears in the above-identified patent and that said Letters Patent is hereby corrected as shown below:

In the Specification

In Column 6, Line 49, delete "particle" and insert -- particles --.

In Column 7, Line 11, delete "be removed" and insert -- be removed or --.

In Column 7, Line 28, delete "an tube" and insert -- a tube --.

In Column 7, Line 28, delete "a achromatic" and insert -- an achromatic --.

In Column 9, Line 46, delete "the produces" and insert -- that produces --.

In Column 10, Line 14, delete "response" and insert -- response. --.

In Column 10, Line 29, delete "dictionary then there" and insert -- dictionary than there --.

In Column 10, Line 66, delete "block 525 the" and insert -- block 530 the --.

In Column 20, Line 50, delete "may a point" and insert -- may have a point --.

In Column 21, Line 2, delete "particles 2005" and insert -- particles 2105 --.

In Column 21, Line 4, delete "2105 may" and insert -- 2100 may --.

In Column 21, Line 5, delete "mask 2015" and insert -- mask 2115 --.

In Column 21, Line 6, delete "subsystem 2010" and insert -- subsystem 2110 --.

In Column 21, Line 11, delete "particles 2005" and insert -- particles 2105 --.

Signed and Sealed this
Eleventh Day of December, 2018

Andrei Iancu
*Director of the United States Patent and Trademark Office*